United States Patent
Rebuffat et al.

(10) Patent No.: US 11,179,398 B2
(45) Date of Patent: Nov. 23, 2021

(54) PURINE DERIVATIVE FOR USE IN THE TREATMENT OR PREVENTION OF DISEASES CAUSED BY A NONSENSE MUTATION

(71) Applicants: MUSÉUM NATIONAL D'HISTOIRE NATURELLE, Paris (FR); CENTRE NATIONAL DE LA RECHERCHE SCIENTIFIQUE, Paris (FR); UNIVERSITÉ LILLE 1, SCIENCES ET TECHNOLOGIES, Villeneuve-d'Asq (FR)

(72) Inventors: Sylvie Rebuffat, Paris (FR); Christine Maulay-Bailly, Paris (FR); Séverine Amand, Bry-sur-Marne (FR); Fabrice Lejeune, Sainghin-en-Weppes (FR)

(73) Assignees: MUSÉUM NATIONAL D'HISTOIRE NATURELLE, Paris (FR); CENTRE NATIONAL DE LA RECHERCHE SCIENTIFIQUE, Paris (FR); UNIVERSITÉ LILLE 1, SCIENCES ET TECHNOLOGIES CITÉ SCIENTIFIQUE, Villeneuve-d'Asq (FR)

( * ) Notice: Subject to any disclaimer, the term of this patent is extended or adjusted under 35 U.S.C. 154(b) by 0 days.

(21) Appl. No.: 16/342,640

(22) PCT Filed: Oct. 20, 2017

(86) PCT No.: PCT/EP2017/076846
§ 371 (c)(1),
(2) Date: Apr. 17, 2019

(87) PCT Pub. No.: WO2018/073413
PCT Pub. Date: Apr. 26, 2018

(65) Prior Publication Data
US 2019/0240228 A1    Aug. 8, 2019

(30) Foreign Application Priority Data
Oct. 21, 2016  (FR) ...................................... 1660229

(51) Int. Cl.
*A61K 31/52*    (2006.01)
*A61K 31/7064*  (2006.01)
*A61P 11/00*    (2006.01)
*A61K 31/4245*  (2006.01)
*A61P 35/00*    (2006.01)

(52) U.S. Cl.
CPC .......... *A61K 31/52* (2013.01); *A61K 31/4245* (2013.01); *A61K 31/7064* (2013.01); *A61P 11/00* (2018.01); *A61P 35/00* (2018.01)

(58) Field of Classification Search
CPC ............................... A61K 31/52; A61P 11/00
See application file for complete search history.

(56) References Cited

FOREIGN PATENT DOCUMENTS

| WO | 03/004511 A2 | 1/2003 |
|---|---|---|
| WO | 2004/009610 A2 | 1/2004 |
| WO | 2014/083327 A1 | 6/2014 |
| WO | WO2015035091 A1 * | 3/2015 |
| WO | 2016/087665 A2 | 6/2016 |

OTHER PUBLICATIONS

Guerin, K. et al., Experimental Eye Research, "Systemic aminoglycoside treatment in rodent models of retinitis pigmentosa", 2008, vol. 87, pp. 197-207 (Year: 2008).*
Written Opinion of the International Searching Authority dated Jan. 30, 2018, issued in corresponding International Application No. PCT/EP2017/076846, filed Oct. 20, 2017, 5 pages.
International Preliminary Report on Patentability dated Apr. 23, 2019, issued in corresponding International Application No. PCT/EP2017/076846, filed Oct. 20, 2017, 1 page.
International Search Report dated Jan. 30, 2018, issued in corresponding International Application No. PCT/EP2017/076846, filed Oct. 20, 2017, 3 pages.
Written Opinion of the International Searching Authority dated Jan. 30, 2018, issued in corresponding International Application No. PCT/EP2017/076846, filed Oct. 20, 2017, 6 pages.
Nagel-Wolfrum, K., et al., "Targeting Nonsense Mutations in Diseases with Translational Read-Through-Inducing Drugs (TRIDs)," Biodrugs 30(2), Apr. 2016, 26 pages.

* cited by examiner

*Primary Examiner* — Bahar Craigo
(74) *Attorney, Agent, or Firm* — Christensen O'Connor Johnson Kindness PLLC

(57) ABSTRACT

The present disclosure relates to 2,6-diaminopurine (DAP) for use in the treatment of a disease caused by a nonsense mutation in a gene, leading to the premature insertion of a UGA stop codon.

Figure 1A:
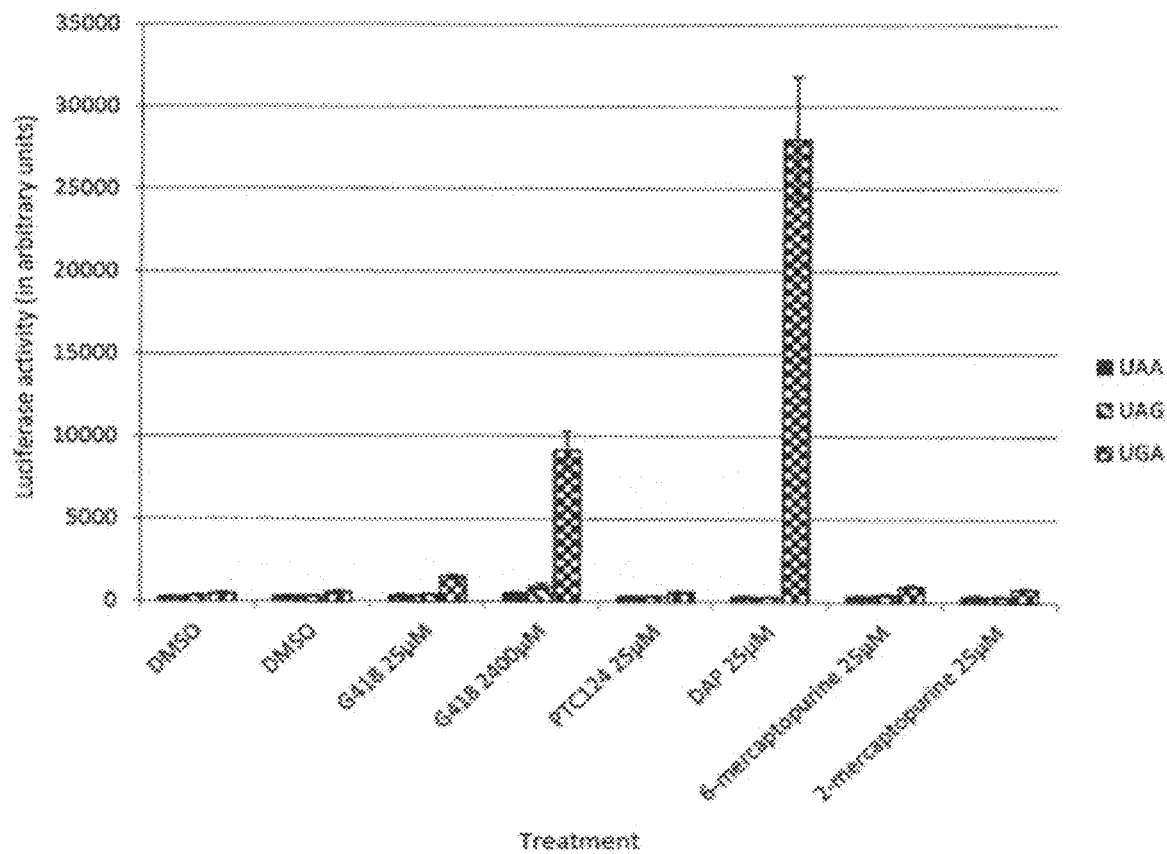

5 Claims, 10 Drawing Sheets
Specification includes a Sequence Listing.

PURINE DERIVATIVE FOR USE IN THE TREATMENT OR PREVENTION OF DISEASES CAUSED BY A NONSENSE MUTATION

The present invention relates to the field of medicaments intended for the treatment of diseases caused by a nonsense mutation. In particular, the invention relates to a new therapeutic application of 2,6-diaminopurine or one of the derivatives thereof for the treatment of diseases caused by a nonsense mutation.

Nonsense mutations are point mutations that lead to a transformation of a codon enabling the incorporation of an amino acid during the translation into a stop codon (UGA, UAG or UAA) causing the interruption of the translation. These mutations are related to approximately ten percent of rare genetic diseases, such as cystic fibrosis, Duchenne muscular dystrophy, haemophilia, dwarfism, etc., or frequent genetic diseases such as certain metabolic disorders, neurological disorders or cancers (Mort et al., 2008).

The consequence of a nonsense mutation is the activation of an mRNA surveillance mechanism that will degrade the mRNA carrying the nonsense mutation. This mechanism is called NMD (for "nonsense-mediated mRNA decay") and prevents the synthesis of a truncated protein (Hug et al., 2016; Kervestin and Jacobson, 2012; Popp and Maquat, 2014; Schweingruber et al., 2013). A nonsense mutation consequently leads to the absence of expression of the gene carrying this mutation.

Several strategies have been developed to correct the consequences of a nonsense mutation (Benhabiles et al., 2016), in particular the inhibition of NMD and/or the activation of readthrough. Readthrough is a mechanism leading to the incorporation, during translation, of an amino acid when the ribosome reaches a premature stop codon. Readthrough is not observed on the physiological stop codon (i.e. the stop codon stopping an open phase of wild reading) in superior eukaryotic cells, even in the presence of readthrough-activating molecules (Welch et al., 2007), with the exception of four genes currently identified that use readthrough on the physiological stop codon thereof (Loughran et al., 2014). The readthrough of a premature stop codon from an mRNA carrying this premature stop codon leads to the synthesis of a protein with a size that is identical to that of the wild protein and featuring at most a single mutated (different) amino acid with respect to the wild protein. Indeed, the amino acid incorporated during the readthrough at the level of the premature stop codon can be different from that present in the wild protein. If this amino acid is not incompatible with the function of the protein, the synthesised protein after readthrough will thus be functional.

Several molecules have been identified as being able to induce readthrough (Benhabiles et al., 2016). In particular, these are certain members of the aminoglycoside family, such as gentamicin or Ia geneticin (also called G418) and molecules that do not belong to this family, such as ataluren (also called PTC 124 or Translama) or amlexanox (Du et al., 2009; Gonzalez-Hilarion et al., 2012; Hermann, 2007; Keeling et al., 2001; Keeling et al., 2006; Welch et al., 2007). However, these molecules have a very limited readthrough efficacy and/or important toxicity. For example, it has not been clearly demonstrated among patients suffering from Duchenne muscular myopathy associated with a nonsense mutation, that ataluren could restore the expression of a gene carrying this nonsense mutation (Fitzhugh and Writer, 2016). G418 is one of the molecules that activates the most effective readthrough (Bidou et al., 2004; Dranchak et al., 2011; Sangkuhl et al., 2004), but the toxicity thereof does not allow for the development thereof for therapeutic purposes (Swan, 1997).

Moreover, Taanman et al. (2003) have shown in vitro from skin fibroblasts sampled from a patient carrying an non-described nonsense mutation of the gene coding deoxyguanosine kinase (mutation of which the deficiency in deoxyguanosine kinase is responsible for the mitochondrial DNA depletion syndrome due to a restricted deoxyguanosine monophosphate (dGMP) and deoxyadenosine monophosphate (dAMP) pool) that dGMP and dAMP supplementation can prevent mitochondrial DNA depletion. Therefore, dGMP or dAMP supplementation enables to reconstitute the pool of deoxyribonucleosides in the cells carrying a nonsense mutation.

Owing to the lack of molecules enabling an effective correction of nonsense mutations, there is a need to identify new molecules having this property.

The Inventors have shown that purine derivatives, in particular 2,6-diaminopurine (designated indifferently as DAP or 2,6-DAP in the following description), feature a selective correcting activity on the UGA stop codon introduced by a nonsense mutation. The Inventors have also shown in vitro that DAP features a correcting activity of this UGA nonsense mutation, significantly higher than that of the G418 compound and of ataluren.

DAP is also known for the use thereof in the treatment of leukaemia (Burchenal et al., 1949) and the antiviral activity thereof (Friend, 1951).

The following formula represents a purine molecule with the numbering of the positions that will be used in the following description:

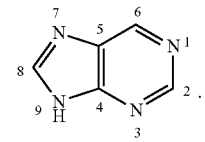

The present invention has the aim of at least one purine derivative, preferably a purine derivative, for the use thereof (intended to be used) in the treatment of a disease caused by a nonsense mutation of a gene leading to the premature introduction of a UGA stop codon.

According to a particularly preferred embodiment of the invention, said purine derivative according to the invention is 2,6-diaminopurine.

2,6-diaminopurine (DAP) has the following formula (I):

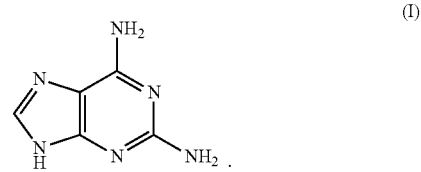 [SMILES: Nc1nc(N)c2nc[nH]c2n1]

Said purine derivative according to the invention can be in the form of a pharmaceutically-acceptable salt.

A pharmaceutically-acceptable salt of the purine derivative according to the invention comprises acid or alkali addition salts of said purine derivative. Appropriate acid addition salts are formed from acids that form non-toxic salts. Examples of acid addition salts include, but are not limited to, acetate, trifluoroacetate, adipate, aspartate, benzoate, besylate, bicarbonate/carbonate, bisulphate/sulphate, borate, tetrafluoroborate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulphate, naphthylate, 2-napsylate, nicotinate, nitrate, orotate, oxalate, palmitate, pamoate, phosphate, monohydrogenated phosphate, dihydrogenated phosphate, pyroglutamate, saccharate, stearate, succinate, tannate, tartrate, tosylate, trifluoroacetate, and xinafoate salts. Appropriate alkali addition salts are formed from alkalis that form non-toxic salts. Examples of alkali addition salts include, but are not limited to aluminium, arginine, benzathine, calcium, choline, diethylamine, diolamine, glycine, lysine, magnesium, meglumine, olamine, potassium, sodium, tromethamine, 2-(diethylamino)-ethanol, ethanolamine, morpholine, 4-(2-hydroxyethyl)-morpholine and zinc salts. Preferably, the pharmaceutically-acceptable salts include hydrochloride/chloride, hydrobromide/bromide, bisulphate/sulphate, nitrate, citrate and acetate.

Said purine derivative according to the invention can be in the form of a solvate.

The term "solvate" is used to describe a purine derivative according to the invention comprising stoichiometric or sub-stoichiometric quantities of one or more molecules of a pharmaceutically-acceptable solvent, such as ethanol.

The term "disease caused by a nonsense mutation of a gene leading to the premature introduction of a UGA stop codon" is used to describe a disease caused by the presence of a nonsense mutation affecting a gene of interest in the germ cells and/or somatic cells; the nonsense mutation is a point mutation of a codon that causes a codon coding an amino acid to change to a UGA stop codon, which leads to the interruption of the translation.

Several diseases due to this nonsense mutation have been described (Keeling et al., 2006; Bidou et al., 2012; Lee and Dougherty, 2012; Kosuga et al., 2016). These diseases can affect different organs, such as the liver, the intestines, the kidneys, the lungs, muscles, bone marrow or the central nervous system.

Diseases due to the nonsense mutation of a gene leading to the premature introduction of an UGA stop codon can be identified by methods implementing the genotyping of the cells of the subject undergoing treatment, more specifically by sequencing or quantification of the expression of the gene of interest. These methods are well known to a person skilled in the art (Baharin et al., 2015; Bladen et al., 2015; Cangül et al., 2015; Carmosino et al., 2016; Csányi et al., 2016; Kosuga et al., 2016; Lin et al., 2016; Roosing et al., 2016; Xia et al., 2016; Zemrani et al., 2016; Zhao et al., 2016). For example, the international application WO 2012/016930 discloses a general method to determine whether a disease is due to this nonsense mutation.

Diseases due to said nonsense mutation include inflammatory diseases due to said nonsense mutation, neurodegeneration diseases due to said nonsense mutation, autoimmune diseases due to said nonsense mutation, cardiovascular diseases due to said nonsense mutation, lung diseases due to said nonsense mutation, cancers due to said nonsense mutation, amyloidosis due to said nonsense mutation, Alzheimer's disease due to said nonsense mutation, atherosclerosis due to said nonsense mutation, gigantism due to said nonsense mutation, dwarfism due to said nonsense mutation, hypothyroidism due to said nonsense mutation, hyperthyroidism due to said nonsense mutation, cystic fibrosis due to said nonsense mutation, obesity due to said nonsense mutation, Parkinson's disease due to said nonsense mutation, Niemann-Pick's disease due to said nonsense mutation, familial hypercholesterolemia due to said nonsense mutation, retinitis pigmentosa due to said nonsense mutation, Marfan's syndrome due to said nonsense mutation, lysosomal storage diseases due to said nonsense mutation, muscular dystrophies due to said nonsense mutation, haemophilia due to said nonsense mutation, the late neuronal ceroid-lipofuscinoses due to said nonsense mutation, beta-thalassemia due to said nonsense mutation, Ehlers-Danlos' syndrome due to said nonsense mutation, Dravet's syndrome due to said nonsense mutation, achromatopsia due to said nonsense mutation, retinitis pigmentosa due to said nonsense mutation, IC-type Usher's syndrome due to said nonsense mutation, musculoskeletal type Ehlers-Danlos' syndrome due to said nonsense mutation, Alagille's syndrome due to said nonsense mutation, Alstrom's syndrome due to said nonsense mutation, antithrombin deficiency due to said nonsense mutation, Carney's complex due to said nonsense mutation, Currarino's syndrome due to said nonsense mutation, Diamond-Blackfan's anaemia due to said nonsense mutation, erythropoietic protoporphyria due to said nonsense mutation, Fabry's disease due to said nonsense mutation, congenital factor XIII deficiency due to said nonsense mutation, Fanconi-Bickel syndrome due to said nonsense mutation, trimethylaminuria due to said nonsense mutation, Gaucher's disease due to said nonsense mutation, hereditary haemorrhagic telangiectasia due to said nonsense mutation, homocystinuria due to said nonsense mutation, Joubert's syndrome due to said nonsense mutation, Krabbe's disease due to said nonsense mutation, L-2-HG aciduria due to said nonsense mutation, methylmalonic acidaemia due to said nonsense mutation, Peters plus syndrome due to said nonsense mutation, Townes-Brocks syndrome caused by said nonsense mutation, Von Willebrand's disease due to said nonsense mutation, Wiskott-Aldrich's syndrome due to said nonsense mutation, Kabuki's syndrome due to said nonsense mutation, Dorfman-Chanarin's disease due to said nonsense mutation, fish eye's disease due to a partial deficiency of lecithin-cholesterol-acyl-transferase due to said nonsense mutation, mucopolysaccharidosis due to said nonsense mutation, coenzyme Q10 deficiency due to said nonsense mutation, Zellweger's syndrome due to said nonsense mutation, colorectal cancer due to said nonsense mutation, congenital enteropathy due to enteropeptidase deficiency due to said nonsense mutation, Peutz-Jeghers syndrome due to said nonsense mutation, Jervell and Lange-Nielsen's syndrome due to said nonsense mutation, Lynch's syndrome due to said nonsense mutation, microvillus atrophy's disease due to said nonsense mutation, xanthinuria due to said nonsense mutation, acidosis due to said nonsense mutation, Alport's syndrome due to said nonsense mutation, Bardet Biedl's syndrome due to said nonsense mutation, Birt-Hogg-Dubé's syndrome due to said nonsense mutation, Dent's disease due to said nonsense mutation, Gitelman's syndrome due to said nonsense mutation, hereditary leiomyomatosis and renal cancer due to said nonsense mutation, Minkowski-Chauffard's disease due to said nonsense mutation, Leber congenital amaurosis due to said nonsense mutation, dibasic protein intolerance with lysinuria due to said nonsense mutation, nephronophtisis due to said nonsense mutation, recessive polycystic kidney disease due to said nonsense mutation, pseudohypoaldosteronism due to said nonsense mutation, renal hypoplasia and dysplasia due to said nonsense mutation, clear cell carcinoma of the kidney due to said nonsense mutation, type 2 papillary renal carcinoma due to said nonsense mutation, Ochoa's syndrome due to said nonsense mutation, Von Hippel-Lindau's disease due to said nonsense mutation, Wilms' tumour due to said nonsense mutation, X-linked hypophosphatemic rickets due to said nonsense mutation, juvenile family hyperuricaemic nephropathy due to said nonsense mutation, Bourneville's tuberous sclerosis due to said nonsense mutation, Finnish nephrotic syndrome due to said nonsense mutation, steroid-resistant idiopathic nephrotic syndrome, Pierson's syndrome due to said nonsense mutation, Denys-Drash's syndrome due to said nonsense mutation, Schimke's syndrome due to said nonsense mutation, primary glucocorticoid resistance due to said nonsense mutation, hypophosphatemic vitamin-resistant rickets due to said nonsense mutation, primary hyperoxaluria of type 1 due to said nonsense mutation, pseudohypoaldosteronism of type 1 (PHA1) due to said nonsense mutation, renal tubular acidosis of type 2 due to said nonsense mutation, Bassen-Kornzweig's syndrome due to said nonsense mutation, Alpers Huttenlocher's syndrome due to said nonsense mutation, carbamoyl phosphate synthetase I deficiency (CPS1) due to said nonsense mutation, cholesterol ester storage disease due to said nonsense mutation, citrin deficiency due to said nonsense mutation, Dubin-Johnson syndrome due to said nonsense mutation, factor V deficiency due to said nonsense mutation, glycogen storage disease due to said nonsense mutation, factor VIII or IX deficiency-haemophilia due to said nonsense mutation, hepatocellular carcinoma due to said nonsense mutation, hepatoerythropoietic porphyria due to said nonsense mutation, family spastic paraplegia caused by said nonsense mutation, hypo-betalipoproteinemia due to said nonsense mutation, constitutional factor XI deficiency due to said nonsense mutation, adult type diabetes in young people due to said nonsense mutation, microcytic hypochromic anaemia due to said nonsense mutation, mitochondrial DNA depletion syndrome due to said nonsense mutation, phenylketonuria due to said nonsense mutation, polycystic liver disease due to said nonsense mutation, porphyria cutanea tarda due to said nonsense mutation, progressive familial intrahepatic cholestasis due to said nonsense mutation, Wilson's disease due to said nonsense mutation, dominant autosomal hypercholesterolemia due to said nonsense mutation, factor XII deficiency due to said nonsense mutation, factor X deficiency due to said nonsense mutation, hypofibrinogenemia due to said nonsense mutation, afibrinogenemia due to said nonsense mutation, factor VII deficiency due to said nonsense mutation, agammaglobulinaemia due to said nonsense mutation, amegakaryocytic thrombocytopenia due to said nonsense mutation, congenital dyserythropoietic anaemia of type 2 due to said non-sense mutation, Duchenne's muscular dystrophies (DMD) and Becker's Muscular dystrophies (BMD) due to said nonsense mutation, centronuclear myopathies due to said nonsense mutation, limb-girdle muscular dystrophy due to said nonsense mutation, Miyoshi's myopathy due to said nonsense mutation, Ullrich's type of congenital muscular dystrophy due to said nonsense mutation, spinal muscular atrophy due to said nonsense mutation, dystrophic epidermolysis bullosa due to said nonsense mutation, Hailey-Hailey's disease due to said nonsense mutation, Helitz's type of junctional epidermolysis bullosa due to said nonsense mutation, Netherton's syndrome due to said nonsense mutation, Hurler's syndrome due to said nonsense mutation, LINCL (Late Infantile Neuronal Ceroid Lipofuscinosis) due to said nonsense mutation, preferably lung cancer and cystic fibrosis due to said nonsense mutation.

According to a specific embodiment, the disease due to said nonsense mutation is selected among cystic fibrosis due to said nonsense mutation, muscular dystrophies due to said nonsense mutation, haemophilia due to said nonsense mutation, beta-thalassemia due to said nonsense mutation, retinitis pigmentosa due to said nonsense mutation, mucopolysaccharidosis due to said nonsense mutation, spinal muscular atrophy due to said nonsense mutation.

In particular, the disease due to said nonsense mutation can by cystic fibrosis due to the nonsense mutation of a gene leading to the premature introduction of a UGA stop codon in the CFTR gene. Cystic fibrosis due to the nonsense mutation of a gene leading to the premature introduction of a UGA stop codon in the CFTR gene can lead, for example, in a non-limited manner, to the following mutations: G27X, W57X, R75X, W202X, W216X, C225X, L320X, W401X, S434X, S466X, S489X, G542X, R553X, G673X, R709X, L732X, G745X, R764X, R785X, R792X, C832X, W846X, R851X, W882X, G1003X, W1063X, W1089X, W1098X, R1102X, R1128X; R1158X, R1162X, S1196X, W1204X, S1206X or W1282X.

The present invention has also aims for a pharmaceutical formulation comprising a purine derivative as defined above, preferably DAP, and a pharmaceutically-acceptable excipient for the use thereof (intended to be used) in the treatment of a disease caused by a nonsense mutation of a gene leading to the premature introduction of a UGA stop codon, such as defined above.

The term "excipient" is used to describe a substance which carries the purine derivative according to the invention in a formulation that gives it properties of stability, of form (for example liquid, solid, capsule), of taste, of dissolution (for example, targeted dissolution in the stomach or in the digestive tract) and of colour.

A "pharmaceutically-acceptable excipient" relates to an excipient that does not cause negative, allergic, or unwanted reactions when it is administered to a subject. This includes all solvents, dispersal media, coatings, antibacterial and antifungal agents, isotonic agents, delayed absorption agents and similar substances. For administration to a human subject, the preparations must meet sterility criteria, pyrogenicity criteria and general purity and safety standards required by regulation authorities. The excipient can, for example, be water.

The present invention also aims for the use of at least one purine derivative or a pharmaceutical formulation as defined above for the preparation of a medicament intended for the treatment of a disease caused by a nonsense mutation of a gene leading to the premature introduction of a UGA stop codon, such as defined above.

The present invention also aims for a method for treating a disease caused by a nonsense mutation of a gene leading to the premature introduction of a UGA stop codon as defined above, comprising the administration of a therapeutically-effective quantity of at least one purine derivative or a pharmaceutical formulation such as defined above to a subject requiring such a treatment.

The terms "treatment" or "to treat" relate to both the therapeutic treatment and the prophylactic or preventive measures taken, the purpose of which is to stop or slow down the progression of a disease due to the nonsense mutation of a gene leading to the premature introduction of a UGA stop codon. Subjects requiring this treatment include subjects who already suffer from a disease due to the nonsense mutation of a gene leading to the premature introduction of a UGA stop codon, those who have a predisposition to a disease due to the nonsense mutation of a gene leading to the premature introduction of a UGA stop codon and those for whom a disease due to the nonsense mutation of a gene leading to the premature introduction of a UGA stop codon must be prevented.

A subject is successfully treated for a disease due to the nonsense mutation of a gene leading to the premature introduction of a UGA stop codon if, after having received a therapeutically-effective quantity of a purine derivative or a pharmaceutical formulation according to the invention, the subject shows an observable or measurable reduction, or the absence of at least one of the following points: reduction of the number of pathogenic cells, reduction of the percentage of pathogenic cells with respect to the total cells, and/or of one or more symptoms associated with the disease due to the nonsense mutation of a gene leading to the premature introduction of a UGA stop codon, or an improvement of the quality of life. The above assessment parameters are easily measurable through routine procedures that are well known to a doctor.

Advantageously, patients are preselected as presenting the nonsense mutation in a gene of interest.

The term "subject" relates to a mammal, preferably a human. According to a preferred embodiment, the subject can be a "patient", i.e. a warm-blooded animal, preferably a human, waiting to receive or already receiving medical care, who has undergone a medical procedure, or who is being monitored for the development of a genetic disease connected to a nonsense mutation of a gene leading to the premature introduction of a UGA stop codon.

A "therapeutically-effective quantity" relates to the quantity of purine derivative or pharmaceutical formulation necessary and sufficient to, without causing unfavourable and significant side effects for the subject, reduce or halt the progression, or the worsening of one or more symptoms of the disease due to a nonsense mutation of a gene leading to the premature introduction of a UGA stop codon, to alleviate the symptoms of the disease due to a nonsense mutation of a gene leading to the premature introduction of a UGA stop codon, and/or to cure the disease due to a nonsense mutation of a gene leading to the premature introduction of a UGA stop codon.

The methods and routes of administration of the purine derivative or of a pharmaceutical formulation described above can be adapted by a person skilled in the art based on the subject and on the purine derivative being used. As an example, the purine derivative according to the invention can be formulated to be administered by oral or nasal route, or by intravenous, intramuscular or subcutaneous injection, preferably orally.

The determination of the dose at which said purine derivative according to the invention is used according to the invention can be conducted with techniques known to a person skilled in the art, for example during clinical trials. This dose will depend on various factors, comprising in particular the activity of the purine derivative according to the invention, the administration mode, the duration of the administration, the duration of the treatment, other medicaments or compounds used in combination with said purine derivative according to the invention, and the age, the gender, the weight, the general state of health and the medical history of the subject undergoing the treatment.

According to an advantageous embodiment, the purine derivative according to the invention is administered to a subject in combination with a compound having a readthrough activity selected from among the group consisting of the alpha anomer of clitocin (6-amino-5-nitro-4-(α-D-ribofuranosylamino)-pyrimidine), the beta anomer of clitocin (6-amino-5-nitro-4-(β-D-ribofuranosylamino)-pyrimidine), ataluren, gentamicin, geneticin, paromomycin and paromomycin derivatives such as NB30; NB54; NB74; NB84, amikacin, tobramycin, pyramycine and pyramycine derivatives such as TC001; TC003; TC007; TC032, kanamycin and kanamycin derivatives such as JL022; JL023, amlexanox, RTC 13 (Lavin, 2013), RTC 14 (Lavin, 2013), 3-(2-4E(1,1 dimethyl propyl)-phenoxy-acetylamino)-benzoic acid, 3-(2-(4-isopropyl-3-methyl-phenoxy)-acetylamino)-benzoic acid, negamycin, tylosin, josamycine, spiramycin, and 3-(2-(4-tert-butyl-phenoxy)-acetylamino)-benzoic acid; preferably the compound having a readthrough activity is selected from the group consisting of the alpha anomer of clitocin (6-amino-5-nitro-4-(α-D-ribofuranosylamino)-pyrimidine), the beta anomer of clitocin (6-amino-5-nitro-4-(β-D-ribofuranosylamino)-pyrimidine) and ataluren.

The present invention has also aims for a compound comprising at least one purine derivative according to the invention, preferably DAP, and a compound having a readthrough activity selected from the group consisting of the alpha anomer of clitocin (6-amino-5-nitro-4-(α-D-ribofuranosylamino)-pyrimidine), the beta anomer of clitocin (6-amino-5-nitro-4-(β-D-ribofuranosylamino)-pyrimidine), ataluren, gentamicin, geneticin, paromomycin and paromomycin derivatives such as NB30; NB54; NB74; NB84, amikacin, tobramycin, pyramycine and pyramycine derivatives such as TC001; TC003; TC007; TC032, kanamycin and kanamycin derivatives such as JL022; JL023, amlexanox, RTC 13 (Lavin, 2013), RTC 14 (Lavin, 2013), 3-(2-4E(1,1 dimethyl propyl)-phenoxy-acetylamino)-benzoic acid, 3-(2-(4-isopropyl-3-methyl-phenoxy)-acetylamino)-benzoic acid, negamycin, tylosin, josamycine, spiramycin, and 3-(2-(4-tert-butyl-phenoxy)-acetylamino)-benzoic acid for their simultaneous, separate or sequential use for the treatment of a disease due to a nonsense mutation of a gene leading to the premature introduction of a UGA stop codon such as defined above; preferably the compound having a readthrough activity is selected from the group consisting of the alpha anomer of clitocin (6-amino-5-nitro-4-(α-D-ribofuranosylamino)-pyrimidine), the beta anomer of clitocin (6-amino-5-nitro-4-(β-D-ribofuranosylamino)-pyrimidine) and ataluren for the simultaneous, separate or sequential use thereof for the treatment of a disease due to a nonsense mutation of a gene leading to the premature introduction of a UGA stop codon such as defined above.

Figure 1B:
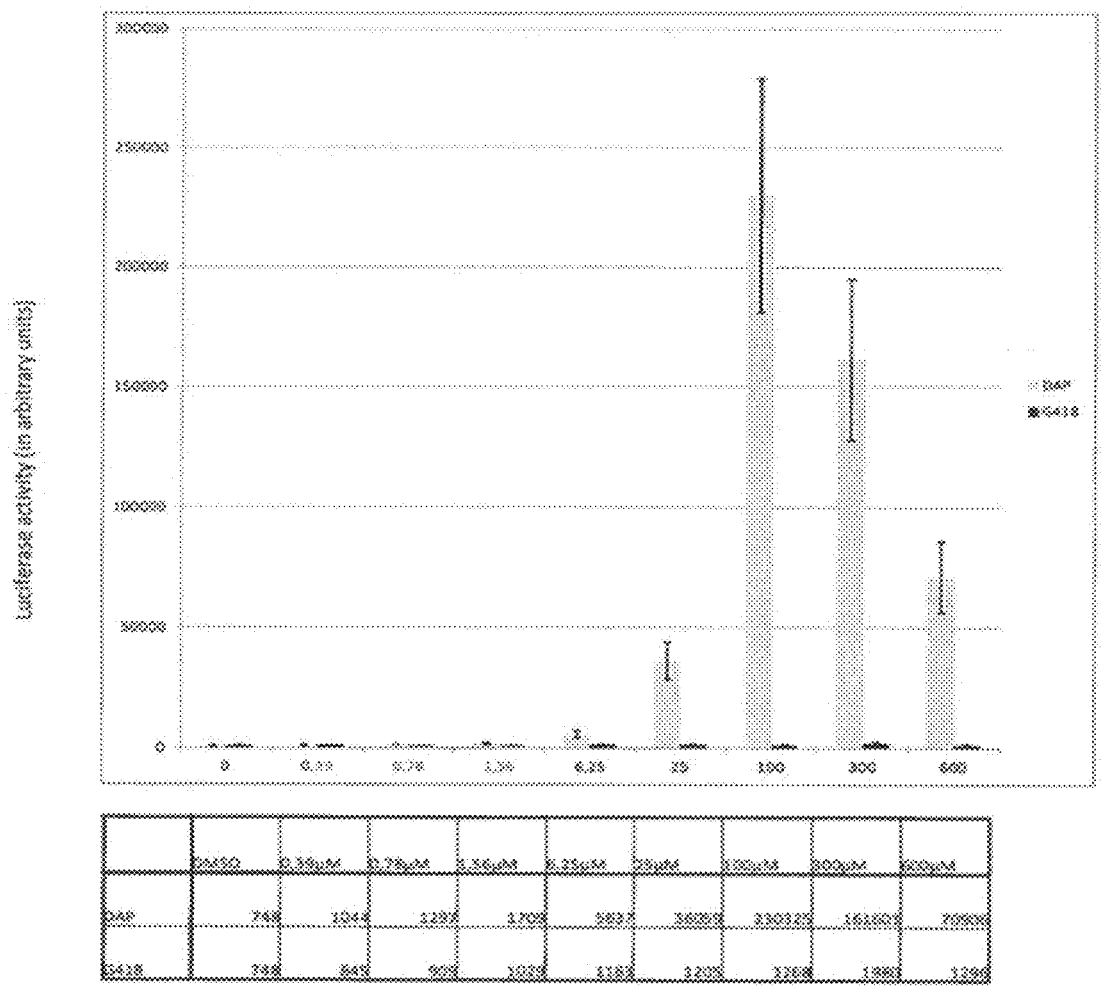

Further to the above provisions, the invention further comprises other non-limiting provisions, which will be revealed in the experimental examples provided hereunder, and in the appended figures:

FIGS. 1A and 1B: Identification of DAP as corrector of the nonsense UGA mutation by screening. 1A. Measurement of the luciferase activity in human HeLa cells expressing a luciferase gene carrying a UAA, UAG or UGA premature stop codon cultivated in the presence of G418 (25 µM, 2400 µM), PTC 124 (ataluren) (25 µM), DAP (25 µM), 6-mercaptopurine (25 µM), 2-mercaptopurine (25 µM) or of DMSO as negative control. DAP at 25 µM shows a correction of the nonsense UGA mutation more than three times more effective than G418 at 2400 µM and eighteen times more effective than G418 at 25 µM under these experimental conditions. In this model, ataluren is ineffective at 25 µM. DAP derivatives (2-mercaptopurine or 6-mercaptopurine) do not have a correcting activity of nonsense mutations. 1B. Measurement of the luciferase activity from HeLa cells expressing a luciferase gene carrying a UGA nonsense mutation in the presence of increasing concentrations of DAP or of G418 (0.39 µM to 600 µM), or of DMSO (negative control). The indicated values show an average of two dose/response curves for each treatment, and the error bars correspond to the calculation of the standard deviation.

Figure 2A:
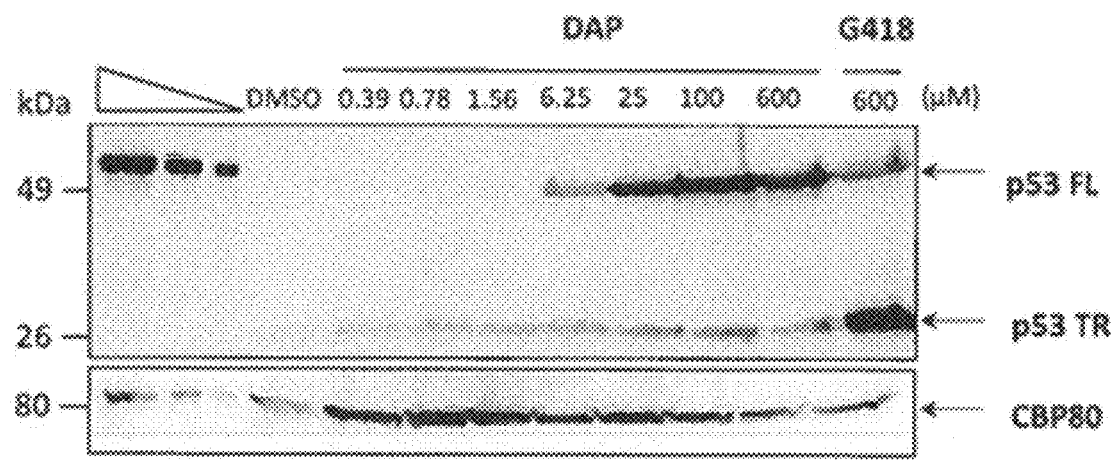
Figure 2B:
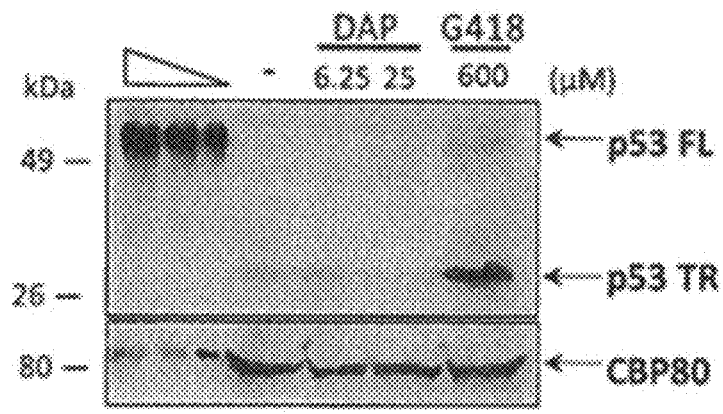
Figure 2C:
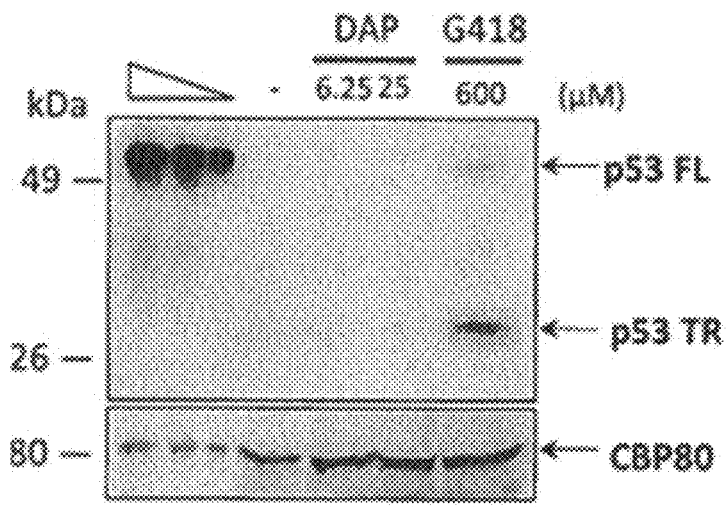

FIGS. 2A-2C: Western blot analysis of the re-expression of the gene TP53 carrying a nonsense mutation. 2A. DAP dose/response experiment and comparison with G418. The proteins of Calu-6 cells (carrying an UGA nonsense mutation at codon 196 in the gene TP53) cultivated in the presence of increasing concentrations of DAP (0.39 µM to 600 µM), of G418 (600 µM) or of DMSO as negative control are purified and analysed by Western blot to detect the protein p53. When these cells are incubated in the presence of DMSO, the expression of the gene TP53 is not detectable by Western blot owing to the presence of the nonsense mutation. In the presence of DAP, the wild-size protein p53 (p53 FL: p53 full length) is detected at 6.25 µM and reaches maximum production at 25 µM. The use of G418 at 600 µM enables the synthesis of a quantity of protein p53 identical to that observed with DAP at 6.25 µM and a greater quantity of truncated protein p53 (p53 TR), the synthesis of which ends at the nonsense mutation. 2B. Analysis of the effect of DAP or of G418 on the Caco-2 cells carrying an UAG mutation at the level of the codon 204 of the gene TP53. DAP does not make it possible to re-express the protein, unlike G418. 2C. Analysis of the effect of DAP or of G418 on the Caov-3 cells carrying an UAA nonsense mutation at the level of the codon 136 of the gene TP53. DAP does not make it possible to re-express the protein p53, unlike G418, which makes it possible for a feeble re-expression. In all the experiments, the protein CBP80 is used as a loading control and the three leftmost bars represent the dilutions in series of a HeLa cell expressing the wild protein p53.

Figure 3:
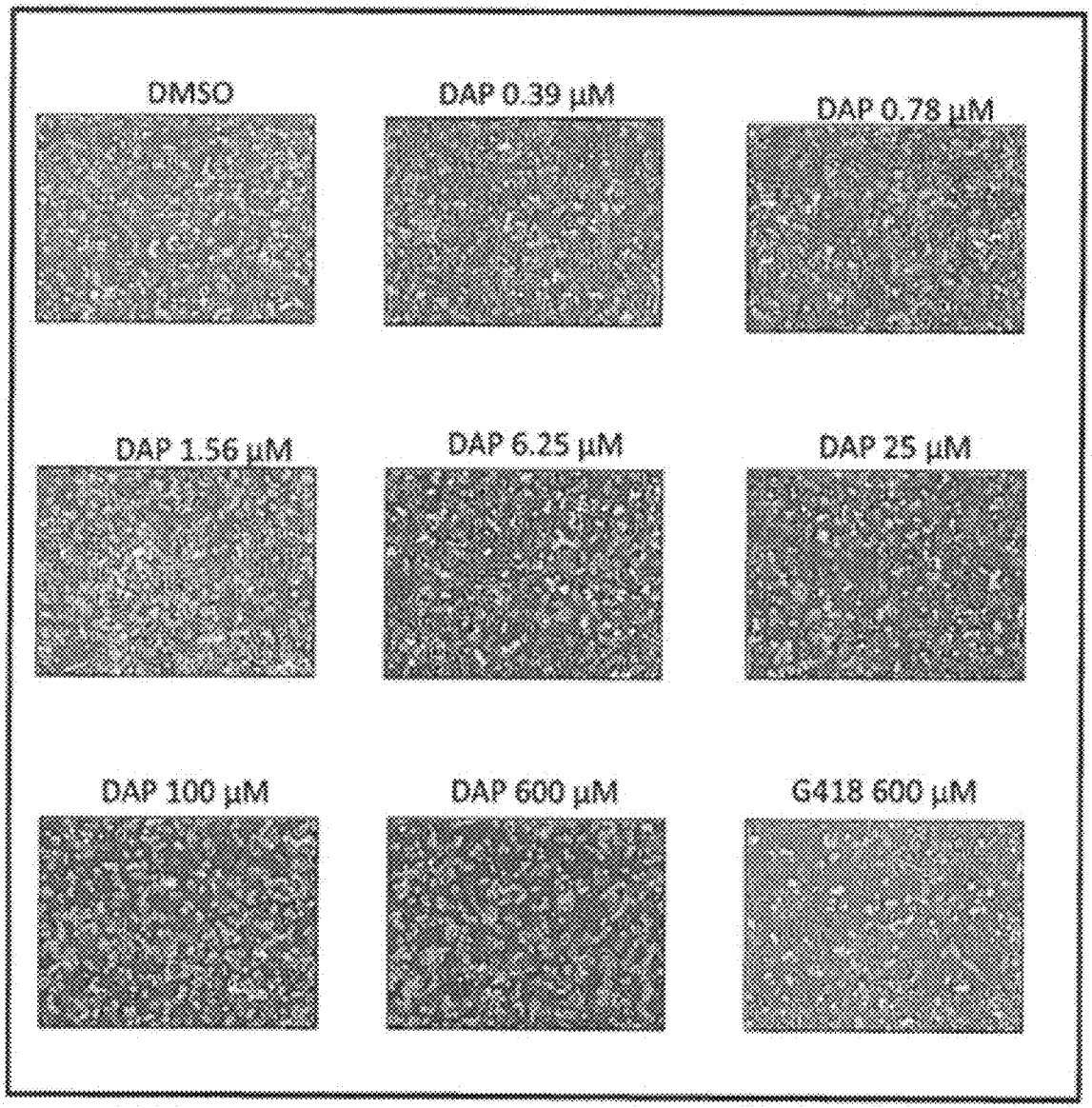

FIG. 3: Effect of DAP on the phenotype of culture cells. White light photography of Calu-6 cells cultivated in the presence of increasing concentrations of DAP (0.39 µM at 600 µM), of G418 (600 µM) or of DMSO as negative control. The acquisition was made with a ZEISS Axiovert 40C microscope and 5× magnification.

Figure 4A:
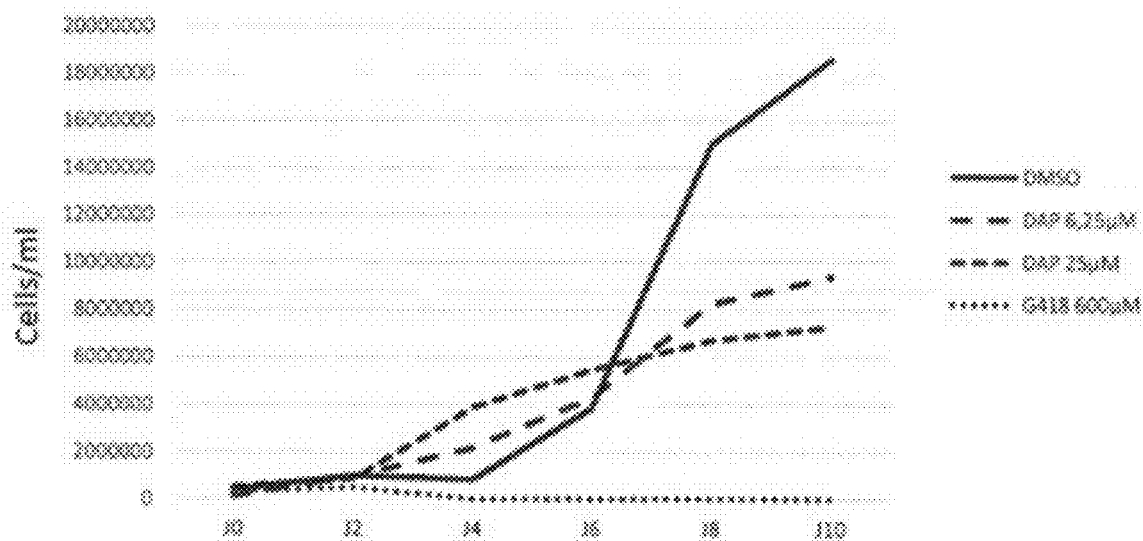
Figure 4B:
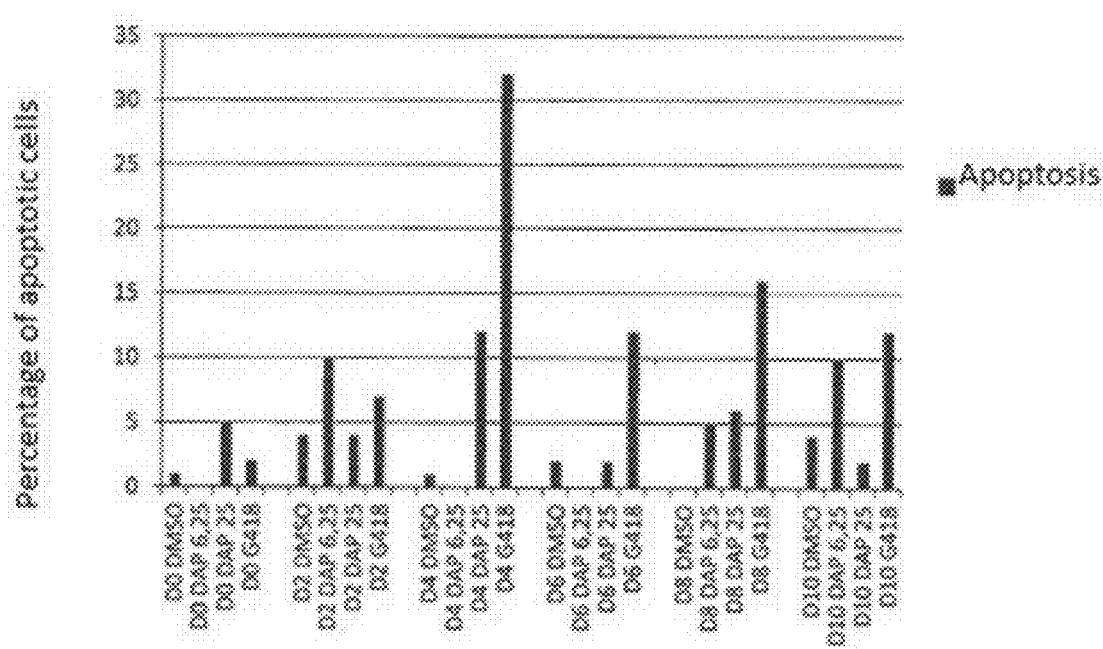

FIGS. 4A and 4B: Measurement of the cellular toxicity of DAP. The Calu-6 cells are cultivated in the presence of DAP (6.25 µM, 25 µM), G418 (600 µM) and DMSO (negative control) for 10 days. The cells were initially seeded at 50,000 cells per well (DO). A cellular count (4A) as well as the measurement of the apoptosis rate (4B) were performed under each condition at D4, D6, D8 and D10.

Figure 5:
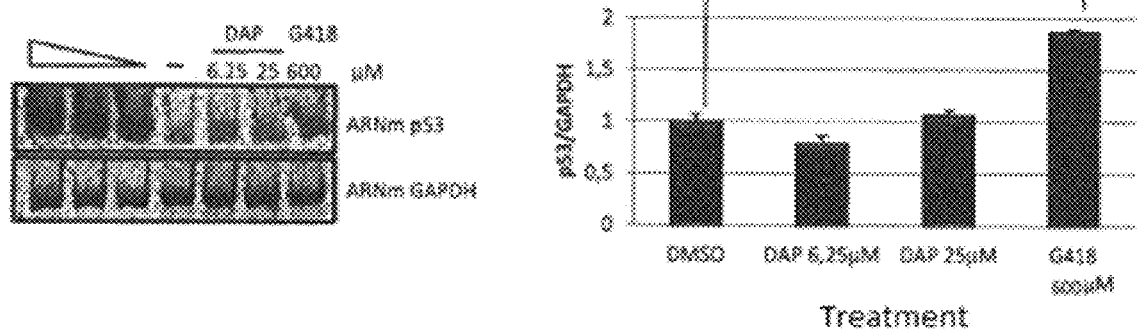

FIG. 5: DAP does not inhibit NMD. The Calu-6 are cultivated for 24 hours in the presence of DAP (6.25 µM or 25 µM), G418 (600 µM), DMSO (negative control). The RNA of the Calu-6 cells is extracted and submitted to a RT-PCR in the presence of a radiolabelled nucleotide to quantify the levels of amplified mRNA p53 and GAPDH (as loading control). The three leftmost bars represent a series of RT dilutions from the mRNA coming from the HeLa cells. A representation in the form of a histogram is shown on the right. *: $p<0.05$.

Figure 6A:
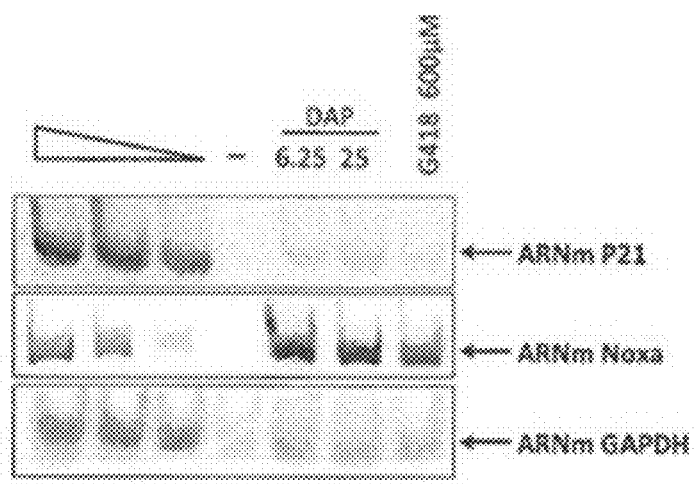
Figure 6B:
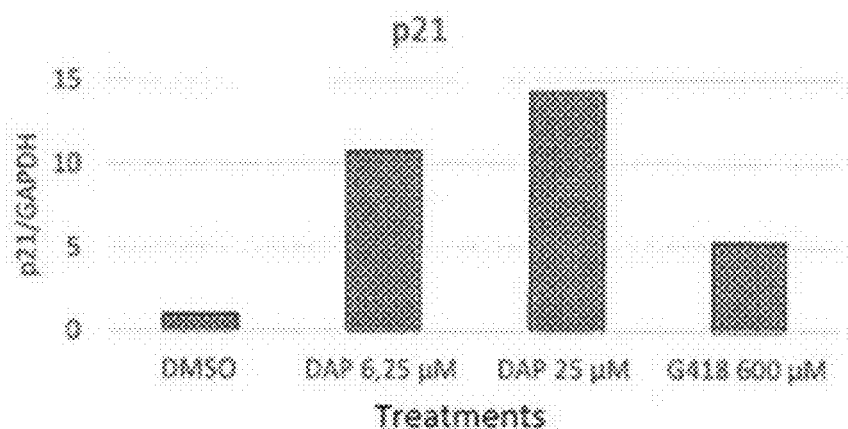
Figure 6C:
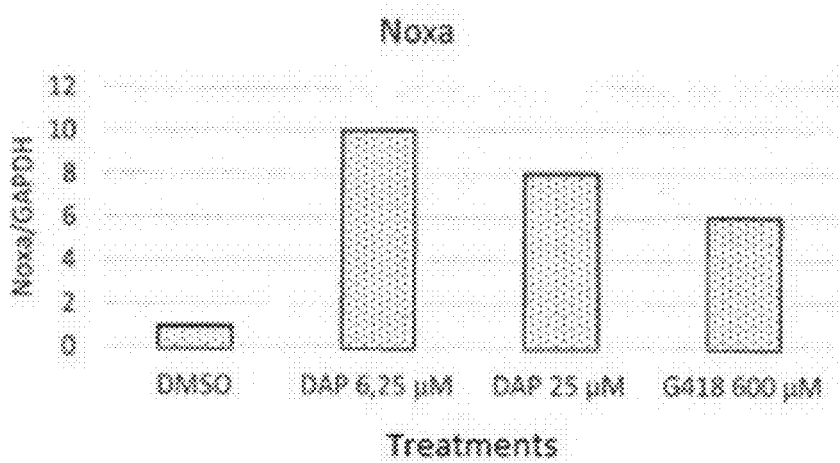

FIGS. 6A-6C: Measurement of the expression of two target genes p53, p21 and Noxa, in the Calu-6 cells after culture in the presence of DAP (6.25 µM or 25 µM), G418 (600 µM) or DMSO (negative control). The NRA of the Calu-6 cells after culture are purified, retro-transcribed and amplified by PCR, then deposited on gel to assess their quantities with respect to the GAPDH (6A). The graphs represent the ratio of the expression level of mRNA p21 (6B), Noxa (6C) with respect to the GAPDH under different culture conditions. In the presence of DAP or G418, the mRNA levels from the p53 target genes increase, reflecting the synthesis of a functional p53 protein in these cells, unlike the treatment of these cells with DMSO.

Figure 7:
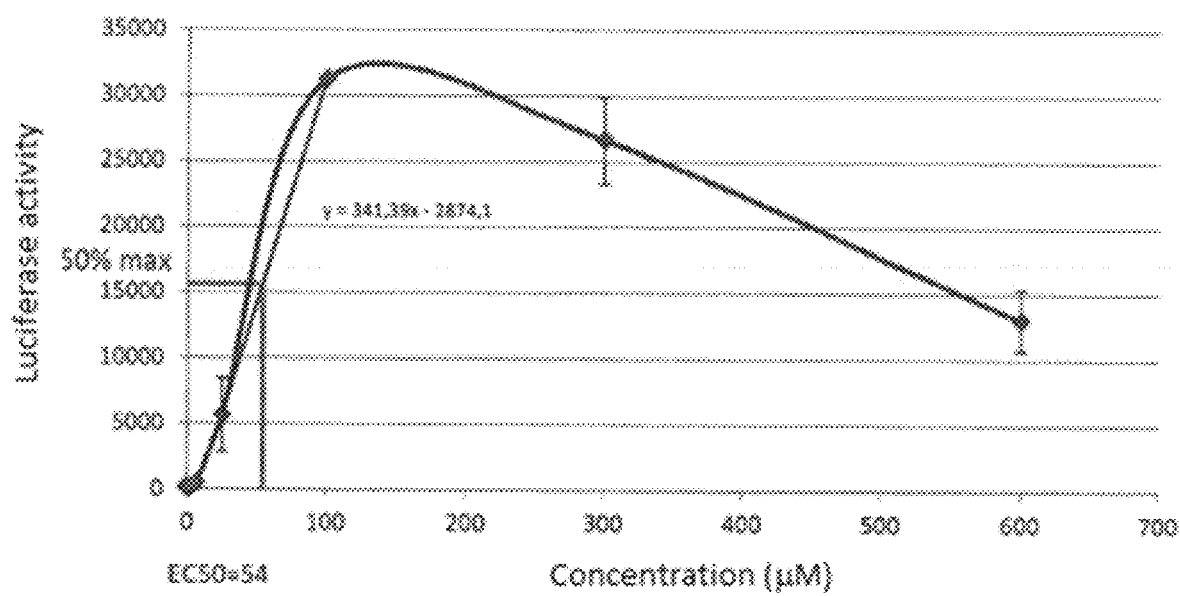

FIG. 7: Characterisation of the optimal concentration of use of DAP. Measurement of the luciferase activity in human HeLa cells expressing a luciferase gene carrying a premature UGA stop codon cultivated in the presence of increasing concentrations of DAP (0-600 µM).

Figure 8:
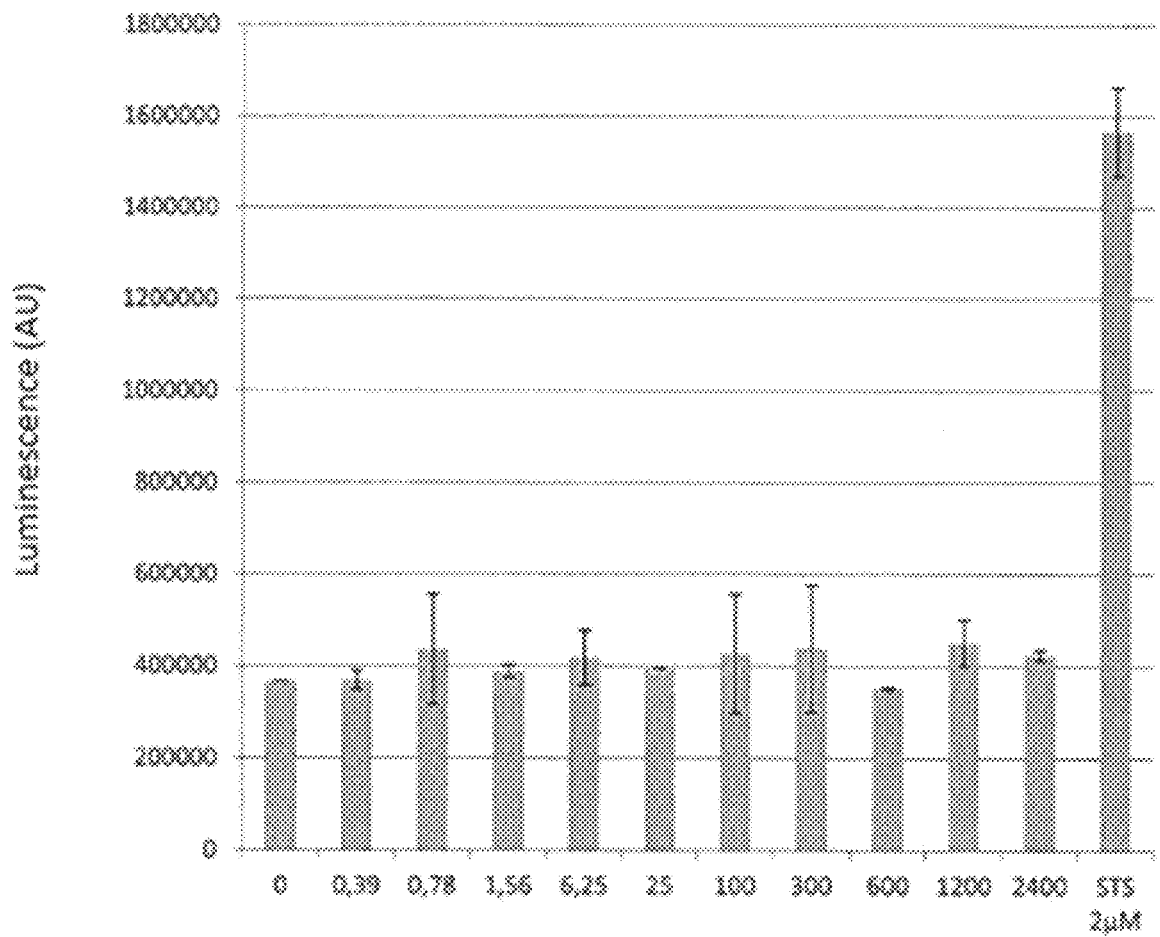

FIG. 8: Measurement of the cytotoxicity of HeLa cells in the presence of DAP at different concentrations with the ToxiLight™ kit (Lonza).

Figure 9A:
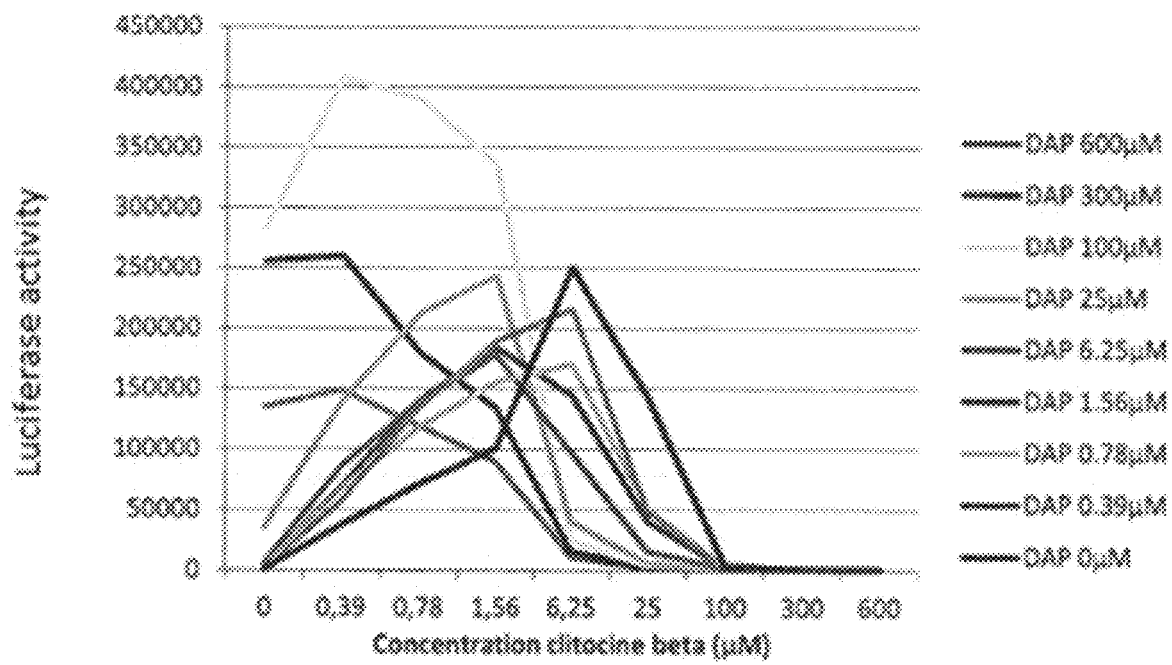
Figure 9B:
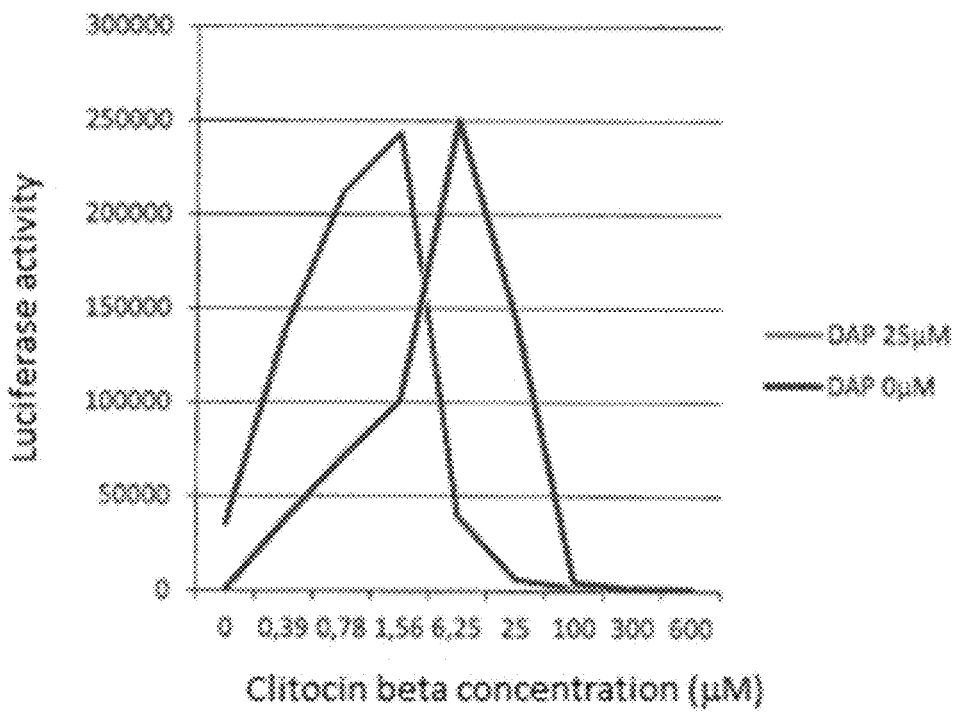

FIGS. 9A and 9B: Synergetic effect of DAP and clitocin. 9A. Measurement of the luciferase activity of human HeLa cells expressing a luciferase gene carrying a premature UGA stop codon cultivated in the presence of increasing concentrations of DAP (curves) and of clitocin (x-axis). 9B. Measurement of the luciferase activity of human HeLa cells expressing a luciferase gene carrying a premature UGA stop codon in the presence of DAP at 0 µM and 25 µM extracted from A illustrating the synergetic effect of DAP and clitocin.

EXAMPLES

1. Identification of 2,6-Diaminopurine (DAP) as Corrector of UGA Nonsense Mutation In order to identify molecules able to effectively correct nonsense mutations in human cells, the gene coding firefly luciferase has been modified by introducing an intron between codons 448 and 449 of the open reading phase, rendering the expression of the luciferase dependent of the splicing, which represents the situation of more than 90% of human genes. A premature stop codon (TAA, TAG or THA) was then introduced in place of codon 109, a position leading to the activation of the NMD ("nonsense-mediated mRNA decay") on that mRNA. It was therefore recreated in the expression context of a spliced gene subject to NMD as is the case in the large majority of human cell genes when they carry a nonsense mutation. The position of the premature stop codon is such that if the protein synthesis stops at the premature stop codon, the synthesised truncated luciferase protein is not functional. A luciferase activity will therefore be measured as superior to the background noise when the luciferase mRNA undergoes the readthrough at the level of the premature stop codon thereof and the intensity of the activity is directly linked to the quantity of synthesised functional luciferase, which is therefore readthrough.

For that purpose, the HeLa cells are transfected with a luciferase construction carrying one of the three nonsense mutations (UAA, UAG, and UGA) using lipofectamin 3000 according to the manufacturer's protocol (Lifetechnologies). The following day, the cells are distributed on a plate with 96 wells and the chemical molecules to be tested are added immediately after an incubation period of 24 hours. The DAP, the 6-mercaptopurine, the 2-mercaptopurine, the ataluren, (PTC 124) were added at a concentration of 25 µM. The G418 was added at a concentration of 25 µM and 2400 µM. The DMSO represents the negative control. The Steady-Lite plus substrate (Perkin Elmer) was then added to the culture medium and the plates were read with a Tristar luminometer (Berthold). Each well is read for 10 seconds and the plate is read twice.

By using these constructions, the 2,6-diaminopurine (DAP) was identified as a molecule able to correct the UGA stop codons much more effectively than G418 or ataluren (PTC 124), which shows no correction activity at this concentration and according to this study model. However, DAP has no effect on the UAG or UAA codons, which means that this molecule is an exclusive corrector of UGA mutations (FIG. 1A). Two DAP derivatives were also tested (2-mercaptopurine and 6-mercaptopurine) but they show no correction activity of nonsense mutations.

A range of dose-response is presented in FIG. 1B for DAP and G418 at a concentration from 0.39 µM to 600 µM in order to show the effectiveness difference between the two molecules in terms of correcting the UGA nonsense mutation. The DMSO represents the negative control. At 6.25 µM, both molecules start to significantly correct the nonsense mutation At this concentration, the DAP induces a correction that is five times higher than G418 according to this model. It should also be noted that DAP reaches the maximum correction effectiveness thereof at 100 µM, unlike G418 which does not reach it at even 600 µM under these experimental conditions. At 100 µM, the correction of the UGA nonsense mutation by DAP is 180 times greater than that obtained by G418 (see FIGS. 4A and 4B).

2. Identification of DAP as a Corrector of the Nonsense UGA Mutation by Readthrough For the purpose of validating the above screening results, the correction of nonsense mutations was measured for endogenous genes carrying nonsense mutations in an immortalised cell line of lung cancer Calu-6 (ATCC, USA) comprising a UGA mutation in the codon 196 of the gene TP53 (FIG. 2A), an immortalised cell line Caco-2 carrying a UAG mutation at the level of codon 204 (FIG. 2B) and an immortalised cell line Caov-3 carrying a UAA nonsense mutation at the level of codon 136 (FIG. 2C).

These cells were cultivated in the presence of increasing concentrations of DAP (0.39 µM; 0.78 µM; 1.56 µM; 6.25 µM; 25 µM; 100 µM; 600 µM), G418 (600 µM) or of DMSO as negative control for 20 hours. The presence of the truncated form (p53 TR) and of the full form (FL) of protein p53 is revealed by Western Blot. The proteins are extracted from the cell in a lysis buffer, then analysed by SDS-PAGE gel at 10% as previously described in Gonzalez-Hilarion et al. (2012). Briefly, after migration, the proteins are transferred onto a nitrocellulose membrane and placed in the presence of an anti-p53 antibody (D01; Santa-Cruz), and then of a secondary anti-mouse antibody (Jackson Immuno Research). The proteins were finally revealed using the SuperSignal West Femto Maximum Sensitivity substrate.

The results (FIGS. 2A-2C) show that DAP is capable of restoring the expression of genes carrying the UGA-type nonsense mutation, thereby validating the screening results.

The minimal concentration enabling this re-expression on these cell lines is of 6.25 µM for which the quantity of synthesised protein is similar to the quantity obtained with G418 at the concentration of 600 µM, which is a concentration generally used to demonstrate readthrough by G418 (Bidou et al., 2004). At 25 µM of DAP, a synthesis of readthrough protein greater than with G418 is achieved.

3. DAP Shows No or Little Toxicity at Concentrations Enabling the Correction of UGA Mutations Calu-6 cells treated with DAP or G418 at different concentrations, as described above, are observed under white light with a microscope (5× magnification) to visualise the phenotype changes of the cells.

The results are shown in FIG. 3. Up to 25 µM of DAP, the phenotype of the cells is similar to that of cells exposed to DMSO. From 600 µM of DAP, more dying cells (round appearance) are observed, which represents a situation that is very similar to that observed by incubating cells with G418 at the concentration of 600 µM. This result suggests that under experimental conditions, DAP has no or little toxicity at a concentration of 6.25 µM or 25 µM, which are sufficient concentrations to achieve the readthrough of UGA premature stop codons (FIGS. 2A-2C).

4. Cellular Growth and Apoptosis Measurement

In order to study the toxicity of DAP, the growth of Calu-6 cells was monitored in the presence or in the absence of DAP or G418.

50,000 Calu-6 cells are seeded on plates with 6 wells in the presence of DAP (6.25 µM or 25 µM), G418 (600 µM), DMSO (negative control). Every 48 hours, for each treatment condition, the cells were retrieved after digestion with trypisin and counted with a TALI cytometer (Lifetechnologies) and analysed for apoptosis as described previously in Jia et al., 2015. Briefly, the cells are removed from their support using typisin and centrifuged for 5 minutes at 200 g. The cell pellet is thus lysed and treated to detect apoptotic cells using the Tali® Apoptosis Kit—Annexin V Alexa Fluor® 488 & Propidium Iodide (Invitrogen).

The results are represented in FIGS. 4A and 4B. Unlike the cells treated with G418, the cells treated with both concentrations of DAP show a constantly positive grow rate despite a slowing down of the growth, in particular at 25 µM (FIG. 4A). This result indicates that the number of cells undergoing division is greater than the number cells of which the cellular cycle has stopped or of dead cells.

In addition, contrary to the wells cultivated in the presence of G418, of which the percentage of apoptotic cells is in excess of 30% from the 4th day of culture, in wells treated with DAP, the rate does not exceed 15% (FIG. 4B).

These results show that DAP causes a slight slowing down of the cellular cycle, but without significant toxicity.

5. DAP Does Not Cause an Inhibition of NMD

In order to study how DAP enables to correct UGA nonsense mutations, it was determined whether this molecule could inhibit NMD. The level of mRNA carrying a UGA nonsense mutation (mNRA p53 in Calu-6 cells) was measured in the absence or presence of DAP.

Calu-6 cells are cultivated in the presence of DAP (6.25 µM, 25 µM), G418 (600 µM) and DMSO as negative control for 24 hours. The RNAs were purified with RNazol (MRC) and underwent a RT-PCR as described in Gonzalez-Hilarion et al. (2012). The resulting cDNA were then amplified after 35 cycles of PCR using the p53 sense primer (5'-ATGTGCT-CAAGACTGGCGC-3'; SEQ ID NO: 1), antisense p53 (5'-GACAGCATCAAATCATCC-3'; SEQ ID NO: 2), sense GAPDH (5'-CATTGACCTCAACTACATGG-3'; SEQ ID NO: 3), antisense GAPDH (5'-GCCATGCCAGT-GAGCTTCC-3'; SEQ ID NO: 4).

The results show that DAP is not capable of stabilising an mRNA carrying a premature stop codon, thereby showing that DAP is not an NMD inhibitor (FIG. 5).

6. The Protein Readthrough by DAP is Functional

For the purpose of showing that the protein readthrough in the presence of DAP is functional, the expression of two target genes of the transcription factor p53, p21 and Noxa was measured in Calu-6 cells. The increase of the observed expression thereof indicates that the synthesised p53 protein is capable of activating the target genes and is therefore functional.

As described above, the Calu-6 cells are cultivated in the presence of DAP (6.25 μM, 25 μM), G418 (600 μM) and DMSO as negative control for 20 hours. The RNAs were purified with RNazol (MRC) and underwent a RT-PCR as described in Gonzalez-Hilarion et al. (2012). The resulting cDNA were then amplified after 35 cycles of PCR using the p21 mRNA primers (sense: 5'-GGAAGAC-CATGTGGACCTGT-3'; SEQ ID NO: 5; antisense 5'-GACAAGTGGGGAGGAGGAAG-3'; SEQ ID NO: 6); GADD45 mRNA (sense: 5'-GGAGGAGGAGGATGA-CATCG-3'; SEQ ID NO: 7; antisense 5'-GCTTGCAGTCAGTCTCACTC-3'; SEQ ID NO: 8); NOXA mRNA (sense: 5'-CAGAGCTG-GAAGTCGAGTGT-3'; SEQ ID NO: 9; antisense 5'-AG-GAGTCCCCTCATGCAAGT-3'; SEQ ID NO: 10).

The results presented in FIGS. 6A-6C show that from 6.25 μM of DAP, the expression of the target genes of p53 increases, which indicates that the p53 protein synthesised in these cells in the presence of DAP is functional. It is observed the G418 also makes it possible for a functional expression of p53, but less important than with DAP. This suggests that the incorporated amino acid or amino acids in the presence of G418 at the nonsense mutation position is/are less compatible with the function of the p53 protein than when DAP induces the readthrough.

7. Compensatory Mutation Test on Bacteria

Equipment and Method

The bacterial strains used in this test are *Salmonella typhimurium* TA1535, TA1537, TA98, TA100 and TA102 strains, supplied by Moltox (Molecular Toxicology, INC, Boone, N.C. 28607, USA) or by "Culture Collections of Public Health England" (Porton Down, Salisbury SP4 0JG, UK).

The test was conducted in the absence or presence of a metabolic solution called S9 mixture (S9 mixture of rat liver treated with aroclor. The concentration of the S9 fraction in the S9 mixture is of 10%). The composition of the S9 mixture is provided in Table 1 below.

TABLE 1

Composition of the S9 metabolic activation solution

| Ingredient | Final concentration |
|---|---|
| Glucose-6-phosphate | 5 mM |
| NADP | 4 mM |
| KCl | 33 mM |
| $MgCl_2$ | 8 mM |
| pH 7.4 Sodium phosphate buffer | 100 mM |
| S9 fraction (Molecular Toxicology, INC, Boone, NC 28607, USA) | 10% (v/v) |
| Water | to volume |

The final concentrations that were used are 0.5; 1.4; 4.1; 12.3; 37; 111.1; 333.3 and 1000 μg/well for each of the bacterial strains, in the presence or absence of the S9 mixture. The solvent used is dimethyl sulfoxide (DMSO), the volume containing the molecule to be tested or DMSO alone is of 25 μl per well.

The positive controls used are:

For the tests conducted in the presence of the S9 mixture, 2-anthranine at 1 μg/well for the TA98, TA100 and TA1535 strains or of 5 μg/well for the TA102 or TA1537 strains.

For the tests conducted in the absence of the S9 mixture, different positive controls were used: 2-nitrofluorene at 0.25 μg/well for the TA98 strain, sodium azide at 1 μg/well for the TA100 strain or at 0.5 μg/well for the TA1535 strain, mitomycin C at 0.25 μg/well for the TA102 strain or 9-aminoacridine at 25 μg/well for the TA1537 strain.

The experiments were conducted once in triplicate.

The treatment in the absence of presence of the S9 mixture was conducted by adding it directly in the wells.

Results

The results are presented in Tables 2 and 3. No precipitate was observed in the wells during the counting of the revertants for any of the doses tested, in any strain, both in the presence and in the absence of the S9 mixture.

TABLE 2

Main test without metabolic activation - method of direct incorporation in the well

| strain | compound | dose (μg/well) | average number of revertants per well | standard deviation | treated/solvent ratio | individual revertant per colony |
|---|---|---|---|---|---|---|
| TA1535 | 2,6 DAP | 1000.0 | 0.0 | 0.0 | 0.0 | 0.0.0 |
|  |  | 333.3 | 3.3 | 1.2 | 1.3 | 4.2.4 |
|  |  | 111.1 | 3.7 | 1.5 | 1.4 | 5.4.2 |
|  |  | 37.0 | 1.3 | 0.6 | 0.5 | 1.2.1 |
|  |  | 12.3 | 4.0 | 3.0 | 1.5 | 4.7.1 |
|  |  | 4.1 | 2.3 | 3.2 | 0.9 | 0.6.1 |
|  |  | 1.4 | 2.3 | 1.5 | 0.9 | 1.2.4 |
|  |  | 0.5 | 3.3 | 4.9 | 1.3 | 0.9.1 |
|  | DMSO |  | 2.7 | 1.2 |  | 2.4.2 |
| TA1537 | 2,6 DAP | 1000.0 | 0.0 | 0.0 | 0.0 | 0.0.0 |
|  |  | 333.3 | 1.3 | 0.6 | 0.5 | 2.1.1 |
|  |  | 111.1 | 3.0 | 3.5 | 1.1 | 1.1.7 |
|  |  | 37.0 | 3.3 | 2.9 | 1.3 | 5.0.5 |
|  |  | 12.3 | 2.3 | 2.3 | 0.9 | 5.1.1 |
|  |  | 4.1 | 1.3 | 2.3 | 0.5 | 4.0.0 |
|  |  | 1.4 | 1.7 | 0.6 | 0.6 | 2.1.2 |
|  |  | 0.5 | 1.3 | 2.3 | 0.5 | 0.0.4 |
|  | DMSO |  | 2.7 | 2.3 |  | 4.4.0 |

TABLE 2-continued

Main test without metabolic activation - method of direct incorporation in the well

| strain | compound | dose (µg/well) | average number of revertants per well | standard deviation | treated/solvent ratio | individual revertant per colony |
|---|---|---|---|---|---|---|
| TA98 | 2,6 DAP | 1000.0 | 3.0 | 2.6 | 0.4 | 2.6.1 |
| | | 333.3 | 7.3 | 4.2 | 0.9 | 6.4.12 |
| | | 111.1 | 6.0 | 4.6 | 0.8 | 5.2.11 |
| | | 37.0 | 5.3 | 2.9 | 0.7 | 7.7.2 |
| | | 12.3 | 8.3 | 2.9 | 1.0 | 5.10.10 |
| | | 4.1 | 9.3 | 2.1 | 1.2 | 11.7.10 |
| | | 1.4 | 11.0 | 1.7 | 1.4 | 12.12.9 |
| | | 0.5 | 10.7 | 0.6 | 1.3 | 11.10.11 |
| | DMSO | | 8.0 | 3.5 | | 12.6.6 |
| TA100 | 2,6 DAP | 1000.0 | 0.0 | 0.0 | 0.0 | 0.0.0 |
| | | 333.3 | 28.3 | 16.2 | 0.7 | 19.19.47 |
| | | 111.1 | 36.3 | 8.1 | 0.9 | 42.27.40 |
| | | 37.0 | 43.7 | 6.8 | 1.0 | 46.36.49 |
| | | 12.3 | 40.7 | 5.5 | 1.0 | 47.38.37 |
| | | 4.1 | 42.0 | 8.7 | 1.0 | 32.47.47 |
| | | 1.4 | 44.3 | 4.0 | 1.1 | 42.49.42 |
| | | 0.5 | 42.0 | 5.6 | 1.0 | 48.41.37 |
| | DMSO | | 42.0 | 7.9 | | 48.33.45 |
| TA102 | 2,6 DAP | 1000.0 | 3.3 | 3.2 | 0.1 | 2.7.1 |
| | | 333.3 | 50.0 | 4.6 | 1.5 | 51.45.54 |
| | | 111.1 | 54.3 | 16.3 | 1.6 | 47.43.73 |
| | | 37.0 | 42.3 | 6.0 | 1.2 | 36.43.48 |
| | | 12.3 | 35.0 | 2.0 | 1.0 | 33.37.35 |
| | | 4.1 | 37.0 | 2.6 | 1.1 | 36.35.40 |
| | | 1.4 | 34.3 | 5.9 | 1.0 | 41.30.32 |
| | | 0.5 | 32.0 | 5.6 | 0.9 | 37.26.33 |
| | DMSO | | 34.3 | 3.2 | | 33.32.38 |
| TA1535 | NaN3 | 0.5 | 206.7 | 10.3 | 77.5 | 218.198.204 |
| TA1537 | 9AA | 25.0 | 553.7 | 65.2 | 207.6 | 583.599.479 |
| TA98 | 2NF | 0.25 | 63.7 | 4.5 | 8.0 | 64.59.68 |
| TA100 | NaN3 | 1.0 | 232.3 | 20.7 | 5.5 | 210.236.251 |
| TA102 | MMC | 0.25 | 243.3 | 11.7 | 7.1 | 241.233.256 |

Abbreviations of positive controls:
NaN3 sodium azide
9AA 9-aminoacridine
2NF 2-nitrofuorene
MMC mitomycin C

TABLE 3

Main test with metabolic activation - direct incorporation method in the well

| strain | compound | dose (µg/well) | average number of revertants per well | standard deviation | treated/solvent ratio | individual revertant per colony |
|---|---|---|---|---|---|---|
| TA1535 | 2,6 DAP | 1000.0 | 0.0 | 0.0 | 0.0 | 0.0.0 |
| | | 333.3 | 14.7 | 5.0 | 4.4 | 14.10.20 |
| | | 111.1 | 13.3 | 2.1 | 4.0 | 11.14.15 |
| | | 37.0 | 8.3 | 2.1 | 2.5 | 10.9.6 |
| | | 12.3 | 4.0 | 2.0 | 1.2 | 6.4.2 |
| | | 4.1 | 3.3 | 2.9 | 1.0 | 5.5.0 |
| | | 1.4 | 2.0 | 2.0 | 0.6 | 4.2.0 |
| | | 0.5 | 3.0 | 1.7 | 0.9 | 4.4.1 |
| | DMSO | | 3.3 | 2.1 | | 1.4.5 |
| TA1537 | 2,6 DAP | 1000.0 | 0.0 | 0.0 | 0.0 | 0.0.0 |
| | | 333.3 | 0.7 | 0.6 | 0.3 | 1.1.0 |
| | | 111.1 | 4.0 | 0.0 | 1.5 | 4.4.4 |
| | | 37.0 | 3.7 | 1.5 | 1.4 | 5.2.4 |
| | | 12.3 | 4.0 | 2.0 | 1.5 | 6.4.2 |
| | | 4.1 | 2.0 | 0.0 | 0.8 | 2.2.2 |
| | | 1.4 | 1.7 | 0.6 | 0.6 | 2.1.2 |
| | | 0.5 | 1.3 | 0.6 | 0.5 | 1.2.1 |
| | DMSO | | 2.7 | 1.2 | | 2.2.4 |

TABLE 3-continued

Main test with metabolic activation - direct incorporation method in the well

| strain | compound | dose (μg/well) | average number of revertants per well | standard deviation | treated/solvent ratio | individual revertant per colony |
|---|---|---|---|---|---|---|
| TA98 | 2,6 DAP | 1000.0 | 6.3 | 2.5 | 0.9 | 6.9.4 |
| | | 333.3 | 10.0 | 1.0 | 1.4 | 9.11.10 |
| | | 111.1 | 13.0 | 2.6 | 1.9 | 10.14.15 |
| | | 37.0 | 9.3 | 0.6 | 1.3 | 9.10.9 |
| | | 12.3 | 9.3 | 4.0 | 1.3 | 7.7.14 |
| | | 4.1 | 7.7 | 3.2 | 1.1 | 10.4.9 |
| | | 1.4 | 6.7 | 4.9 | 1.0 | 10.1.9 |
| | | 0.5 | 12.3 | 5.5 | 1.8 | 15.6.16 |
| | DMSO | | 7.0 | 5.0 | | 7.12.2 |
| TA100 | 2,6 DAP | 1000.0 | 0.0 | 0.0 | 0.0 | 0.0.0 |
| | | 333.3 | 53.7 | 6.7 | 1.3 | 57.46.38 |
| | | 111.1 | 51.3 | 14.7 | 1.3 | 68.46.40 |
| | | 37.0 | 49.0 | 4.4 | 1.2 | 47.46.54 |
| | | 12.3 | 53.7 | 8.0 | 1.3 | 53.46.62 |
| | | 4.1 | 49.0 | 3.5 | 1.2 | 53.47.47 |
| | | 1.4 | 41.0 | 11.5 | 1.0 | 54.32.37 |
| | | 0.5 | 43.3 | 7.6 | 1.1 | 40.52.38 |
| | DMSO | | 40.0 | 18.2 | | 28.31.61 |
| TA102 | 2,6 DAP | 1000.0 | 18.0 | 3.5 | 0.4 | 20.20.14 |
| | | 333.3 | 69.3 | 8.5 | 1.5 | 78.61.69 |
| | | 111.1 | 44.0 | 10.6 | 1.0 | 56.36.40 |
| | | 37.0 | 48.3 | 3.1 | 1.1 | 49.45.51 |
| | | 12.3 | 47.3 | 4.5 | 1.1 | 52.43.47 |
| | | 4.1 | 41.3 | 10.1 | 0.9 | 53.36.35 |
| | | 1.4 | 41.7 | 3.5 | 0.9 | 45.38.42 |
| | | 0.5 | 42.0 | 13.1 | 0.9 | 36.33.57 |
| | DMSO | | 45.0 | 8.7 | | 51.35.49 |
| TA1535 | 2AM | 1.0 | 137.7 | 11.7 | 41.3 | 148.125.140 |
| TA1537 | 2AM | 5.0 | 36.0 | 5.3 | 13.5 | 40.38.30 |
| TA98 | 2AM | 1.00 | 686.7 | 69.7 | 98.1 | 767.642.651 |
| TA100 | 2AM | 1.0 | 696.0 | 19.2 | 17.4 | 705.674.709 |
| TA102 | 2AM | 5.00 | 91.0 | 3.6 | 2.0 | 95.88.90 |

Abbreviations of positive controls: 2AM: 2-anthramine

A strong toxicity (revealed by the reduction of revertants) is observed in the presence and in the absence of the S9 mixture only at the dose of 1000 μg/well for all the strains, with the exception of the TA98 strain that shows a toxicity of the molecule only in the presence of the S9 mixture. Moreover, the TA1537 strain reveals a toxicity of the molecule starting at the concentration of 333.3 μg/well (i.e. approximately 90 mM) and only in the presence of the S9 mixture.

Regarding the genotoxic effect of DAP, increases of the number of revertants have been observed only in TA1535 strain and only in the presence of the S9 mixture. These increases are greater than the positive response threshold in this strain (i.e. with a ratio that can reach 4.4), observed at concentrations of 111.1 and 333.3 μg/well and they follow a dose effect. In addition, the averages of most of the individual values obtained with doses from 37 to 333.3 μg/well are greater than the values obtained with DMSO alone. These results make it possible to conclude that there is a genotoxic effect of DAP in the TA1535 strain.

No other significant increase of revertants was observed for the other strains in this study.

It must be noted, that a significant increase of revertants was observed with positive controls in the presence and absence of the S9 mixture with respect to DMSO alone, which validates the experimental conditions of the study.

In conclusion, under the experimental conditions of this study, 2,6-DAP presents a mutagenic activity only on the TA1535 strain in the presence of a rat liver metabolic solution.

8. In Vitro Test of the Micronuclei in the Murine Cells L5178Y TK #$^{+/-}$ of Lymphomas Equipment and Method The cells used are L5178Y TK$^{+/-}$ cells obtained from ATCC (American Type Culture Collection, Manassas, USA) via Biovalley (Marne-la-Vallée, France) for the induction of micronuclei. The test was conducted in the absence or in the presence of the metabolic mixture S9 wherein the S9 fraction (Moltox; Molecular Toxicology, INC, Boone, N.C. 28607, USA) represents 2% of the culture medium. The composition of the S9 mixture is provided in Table 4 below.

TABLE 4

| Composition of the S9 mixture | |
|---|---|
| Ingredient | Volume(s) |
| Glucose-6-phosphate (180 mg/mL) | 1 |
| NADP (25 mg/mL) | 1 |
| KCl (150 mg/mL) | 1 |
| S9 fraction (final concentration in S9 mix 40% (v/v)) | 2 |

In the test with metabolic activation, the culture medium is supplemented with 5% of the S9 mixture, thus the final concentration of S9 in the treated medium is of 2%.

The tested DAP doses are 0.01; 0.02; 0.04; 0.07; 0.15; 0.29; 0.58; 1.17; 2.33 and 4.66 mM. The maximum concentration was determined by the solubility of 2,6-DAP in DMSO and the experimental constraints relating to the applicable volume to be tested in the culture medium. For all experimental conditions, DMSO used as solvent of 2,6-DAP will represent only 1% (v/v) of the culture medium.

The concentrations retained as presenting no cytotoxicity of 2,6-DAP for genotoxic analyses are 0.02, 0.04 and 0.07 mM in the absence of the S9 mixture and 0.04, 0.29 and 0.58 mM in the presence of the S9 mixture.

The cells were treated for 24 hours in the absence of the S9 mixture or treated for 3 hours followed by 24 hours of culture without treatment when the S9 mixture was present in the culture medium.

The positive controls used are mitomycin C at a final concentration of 1 µg/ml in the absence of the S9 mixture or cyclophosphamide at a final concentration of 6 µg/ml in the presence of the S9 mixture.

The experiment was conducted and 1000 single-nucleus cells were analysed per culture. Three doses of 2,6-DAP, of DMSO alone or of positive controls in the presence and absence of the S9 mixture were analysed.

The assessment of the cytotoxicity was determined by measuring the doubling of the cell population at the end of the experiment.

Results

The results are indicated in Table 5 below.

TABLE 5

Results obtained with or without the S9 mix mixture

| Treatment conditions | Doses (nM) | DP (% of the control substance) | Number of analysed cells per culture | standard deviation | treated/ solvent ratio |
|---|---|---|---|---|---|
| | 0 | 100 | 1000 | 1 | a) |
| Test without S9 mix | 0.01 | 91 | | | |
| | 0.02 | 121 | 1000 | 2 | 2.0 |
| | 0.04 | 78 | 1000 | 3 | 3.0 |
| | 0.07 | 97 | 1000 | 1 | 1.0 |
| | 0.15 | 21 | | | |
| | 0.29 | # | | | |
| | 0.58 | # | | | |
| | 1.17 | # | | | |
| | 2.33 | # | | | |
| | 4.66 | # | | | |
| | MMC (µg/mL) | | 1000 | 100 | 100.0 ** |
| | 0 | 100 | 1000 | 1 | |
| Test with S9 mix | 0.01 | 76 | | | |
| | 0.02 | 89 | | | |
| | 0.04 | 91 | 1000 | 0 | 0.0 |
| | 0.07 | 74 | | | |
| | 0.15 | 76 | | | |
| | 0.29 | 73 | 1000 | 1 | 1.0 |
| | 0.58 | 54 | 1000 | 0 | 0.5 |
| | 1.17 | 35 | | | |

TABLE 5-continued

Results obtained with or without the S9 mix mixture

| Treatment conditions | Doses (nM) | DP (% of the control substance) | Number of analysed cells per culture | standard deviation | treated/ solvent ratio |
|---|---|---|---|---|---|
| | 2.33 | 44 | | | |
| | 4.66 | 40 | | | |
| | CPA (6 µg/mL) | | 1000 | 60 | 60.0 ** |

0: control (DMSO);
MMC: mitomycin C;
CPA: cyclophosphamide;
DP: doubling of the population;
Statistics: 2*2 contingency table;
***: p < 0.001;
: the cell concentration at the end of the treatment is inferior to that of the beginning of the treatment;
a) raw data obtained with the control is equal to 0, but it has been changed to 1 to make it possible for the calculation of the ratios.

2,6-DAP shows severe cytotoxicity at doses greater than 0.15 mM in the absence of the S9 mixture, as the doubling of the population is reduced from 79 to 100%. In the presence of the S9 mixture, a slight cytotoxicity appears at doses greater than 0.07 mM, as the doubling of the population is reduced from 24 to 64.6%.

No significant increase of the frequency of cells containing micronuclei was observed in comparison with DMSO alone, in the presence or absence of the mixture S9 indicating that there is no genotoxic effect of 2,6-DAP. It must be noted, that the frequency of cells with micronuclei increases significantly in the presence of positive controls, in the presence or absence of the S9 mixture, thereby validating the experimental conditions of the test.

In conclusion, under the experimental conditions of the study, 2,6-DAP does not induce any damage to the chromosomes or cell machinery involved in the cell division in somatic L5178Y TK+/− cells of mammals in the absence or presence of a rat metabolic solution.

9. Measurement of the EC50

The HeLa cells are transfected with the luciferase construction carrying a UGA nonsense mutation described in example 1 by using lipofectamin 3000 according to the manufacturer's protocol (Lifetechnologies). The following day, the cells are distributed on a 96 wells plate and the DAP to be tested is added at different concentrations before an incubation period of 24 hours. The DAP was added at a concentration of 25 µM, 100 µM, 300 µM or 600 µM. The SteadyLite plus substrate (Perkin Elmer) is then added to the culture medium and the plates are read with a Tristar luminometer (Berthold). Each well is read for 10 seconds and the plate is read twice.

The correction effectiveness of the UGA nonsense mutation is represented by the luciferase activity (FIG. 7). The maximum correction effectiveness of the UGA nonsense mutation is achieved with a DAP concentration of 100 µM. The EC50 corresponds to the DAP concentration with which 50% of the maximum luciferase activity. The EC50 of the DAP is of 54 µM.

10. Cytotoxicity Measurement

The HeLa cells are placed in culture on 96-well plates in the presence of different concentrations of DAP (0.39, 0.78, 1.56, 6.25, 25, 100, 300, 600, 1200, 2400 µM). DMSO represents the negative control. Staurosporine (STS) was added as a positive control. After 20 hours of culture at 37° C. and 5% of $CO_2$, the cells are brought to ambient temperature for 5 minutes. 100 µL of AK detection reagent (ToxiLight™ bioassay kit, Lonza) are added in each well to measure the activity of adenylate kinase, an enzyme released in the extracellular medium when the cells are dead. The cells are incubated for 5 minutes with the reagent before the plates are read with a Tristar luminometer (Berthold). No toxicity is observed at different concentrations of DAP used in comparison with the staurosporine treatment (FIG. 8).

11. Synergy with Clitocin

The HeLa cells are transfected with the luciferase construction carrying a UGA nonsense mutation described in example 1 using lipofectamin 3000 according to the manufacturer's protocol (Lifetechnologies). The following day, the cells are distributed on a 96-well plate and incubated for 20 hours in the presence of increasing concentrations of DAP and clitocin combined (0-600 µM). The luciferase activity is measured by adding the SteadyLite plus substrate (Perkin Elmer) to the culture medium and the plates are read with a Tristar luminometer (Berthold). The plate is read twice.

A synergetic effect of DAP and clitocin is observed (FIGS. 9A and 9B), the effect observed for DAP and clitocin combinations being higher than the expected added effect. As an example, the effectiveness of the UGA nonsense mutation observed in the presence of 1.56 µM of clitocin and 25 µM of DAP (measured luminescence: 250,000) is greater than the effectiveness that would be expected for an additive effect of the same mixture of clitocin and DAP (luminescence measured for clitocin at 1.56 µM: 100,000; luminescence measured for DAP alone at 25 µM: 50,000; luminescence expected for an additive effect of clitocin and DAP at these concentrations: 150,000). The maximum effectiveness of the UGA nonsense mutation correction is obtained by combining DAP at 100 µM and clitocin at 0.39 µM.

REFERENCES

Baharin, M. F., et al., 2015, Malaysian J Pathol. 37, 153-158.
Benhabiles, H., et al., 2016, *Nonsense mutation correction in human diseases: an approach for targeted medicine*, Elsevier edn (Publisher: Catherine Van Der Laan).
Bidou, L., et al., 2004, Gene Ther. 11, 619-627.
Bidou, L., et al., 2012, Trends Mol Med. 18, 679-88.
Bladen, C L., et al., 2015, Human Mutation. 36, 395-402.
Burchenal, J. H., et al., 1949, Cancer. 2,1 19.
Cangül, H., et al., 2015, J Clin Res Pediatr Endocrinol. 7, 323-328.
Carmosino, M., et al., 2016, J. Cell. Mol. Med. doi: 10.1111/jcmm.12926.
Csányi, B., et al., 2016, Canadian Journal of Cardiology. 1-8.
Dranchak, P. K, et al., 2011, J Cell Biochem. 112, 1250-1258.
Du, L., et al., 2009, J Exp Med. 206, 2285-2297.
Fitzhugh, M., and Writer, S., 2016, Bioworld. 27, 3-5.
Friend, C, 1951, Proc Soc Exp Biol Med. 78, 150-153.
Gonzalez-Hilarion, S., et al., 2012, Orphanet J Rare Dis. 7, 58.
Hermann, T., 2007, Cell Mol Life Sci. 64, 1841-1852.
Hug, N., et al., 2016, Nucleic Acids Res. 44, 1483-1495.
Jia, J., et al., 2015, Cell Death Differ. 22, 1754-1763.
Keeling, K. M., Du, M., and Bedwell, D. M., 2006. Therapies of Nonsense-Associated Diseases. Nonsense-mediated mRNA Decay—Landes Bioscience Editor: Lynne E. Maquat, 121-136.
Keeling, K. M., et al, 2001, Hum Mol Genet. 10, 291-299.
Kervestin, S., et al., 2012, Nat Rev Mol Cell Biol. 13, 700-712.
Kosuga, M., et al., 2016, Molecular Genetics and Metabolism. 118, 190-197.
Lavin, M. F., 2013, Mol Ther. 21, 1651-1652.
Lee; H. L., & Dougherty, J. P., 2012, Pharmacol. Ther. 136, 227-66.
Lin, F.-J., et al., 2016, Experimental and Therapeutic Medecine. 11, 1249-1252.
Loughran, G., et al., 2014. Nucleic Acids Res. 42, 8928-8938.
Mansoura, M. K., et al., 1999, Hum Gene Ther. 10, 861-875.
Mort, M., et al., 2008, Hum Mutat. 29, 1037-1047.
Popp, M. W., and Maquat, L. E, 2014, Mol Cells. 37, 1-8.
Roosing, S., et al., 2016, Hum Genet. 135, 919-921.
Sangkuhl, K., et al, 2004, Hum Mol Genet. 13, 893-903.
Schweingruber, C, et al., 2013, Biochim Biophys Acta. 1829:612-623.
Swan, S. K., 1997, Semin Nephrol. 17, 27-33.
Taanman, J.-W., et al., 2003, Human Molecular Genetics, 12: 1839-1845.
Welch, E. M., et al., 2007, Nature. 447, 87-91.
Xia, X., et al., 2016, PLoS ONE 11, e0156981.
Zemrani, B., et al., 2016, Eur J Med Res. 21, 19.
Zhao, J., et al, 2016, European Journal of Medical Genetics. 59, 396e400.

The invention claimed is:

1. A method of treating a disease due to a nonsense mutation in a gene leading to the premature introduction of a UGA stop codon, comprising administering to a subject in need thereof a therapeutically effective amount of 2,6-diaminopurine (DAP), wherein said disease is selected from among cystic fibrosis due to said nonsense mutation, muscular dystrophies due to said nonsense mutation, beta-thalassemia due to said nonsense mutation, retinitis pigmentosa due to said nonsense mutation, mucopolysaccharidosis due to said nonsense mutation, spinal muscular atrophy due to said nonsense mutation.

2. The method according to claim 1, wherein said DAP is administered to a subject in combination with a compound having a readthrough activity selected from the group consisting of 6-amino-5-nitro-4-(α-D-ribofuranosylamino)-pyrimidine, 6-amino-5-nitro-4-(β-D-ribofuranosylamino)-pyrimidine, ataluren, gentamicin, geneticin, paromomycin, a paromomycin derivative, amikacin, tobramycin, pyramycine, a pyramycine derivative, kanamycin, a kanamycin derivative, amlexanox, RTC 13 (Lavin, 2013), RTC 14 (Lavin, 2013), 3-(2-4E(1,1 dimethyl propyl)-phenoxy-acetylamino)-benzoic acid, 3-(2-(4-isopropyl-3-methyl-phenoxy)-acetylamino)-benzoic acid, negamycin, tylosin, josamycine, spiramycin, and 3-(2-(4-tert-butyl-phenoxy)-acetylamino)-benzoic acid.

3. The method according to claim 2, wherein the paromomycin derivative is selected from NB30, NB54, NB74, and NB84.

4. The method according to claim 2, wherein the pyramycine derivative is selected from TC001, TC003, TC007, and TC032.

5. The method according to claim 2, wherein the kanamycin derivative is selected from JL022 and JL023.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
atgtgctcaa gactggcgc                                              19

<210> SEQ ID NO 2
<211> LENGTH: 18
```

```
<212> TYPE: DNA
<213> ORGANISM: Artificial Sequence
<220> FEATURE:
<223> OTHER INFORMATION: Primer

<400> SEQUENCE: 2
gacagcatca aatcatcc                                                 18

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cattgacctc aactacatgg                                               20

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
gccatgccag tgagcttcc                                                19

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggaagaccat gtggacctgt                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gacaagtggg gaggaggaag                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggaggaggag gatgacatcg                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
```

```
gcttgcagtc agtctcactc                                            20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cagagctgga agtcgagtgt                                            20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aggagtcccc tcatgcaagt                                            20
```